US012734197B2

(12) United States Patent
Thomson et al.

(10) Patent No.: US 12,734,197 B2
(45) Date of Patent: Sep. 15, 2026

(54) GENERATION OF UNIFORM HEPATOCYTES FROM HUMAN EMBRYONIC STEM CELLS BY INHIBITING TGF-BETA AND METHODS OF MAINTAINING HEPATIC CULTURES

(71) Applicant: Wisconsin Alumni Research Foundation, Madison, WI (US)

(72) Inventors: James A. Thomson, Madison, WI (US); Srikumar Sengupta, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1048 days.

(21) Appl. No.: 17/443,786

(22) Filed: Jul. 27, 2021

(65) Prior Publication Data

US 2022/0016178 A1 Jan. 20, 2022

Related U.S. Application Data

(62) Division of application No. 15/650,595, filed on Jul. 14, 2017, now Pat. No. 11,116,799.

(60) Provisional application No. 62/531,424, filed on Jul. 12, 2017, provisional application No. 62/362,385, filed on Jul. 14, 2016.

(51) Int. Cl.

| | |
|---|---|
| ***A61K 35/407*** | (2015.01) |
| ***C12N 5/071*** | (2010.01) |
| ***C12Q 1/02*** | (2006.01) |
| ***G01N 33/50*** | (2006.01) |
| *C12N 5/00* | (2006.01) |
| *C12Q 1/00* | (2006.01) |

(52) U.S. Cl.

CPC ............ *A61K 35/407* (2013.01); *C12N 5/067* (2013.01); *C12Q 1/02* (2013.01); *G01N 33/50* (2013.01); *C12N 5/00* (2013.01); *C12N 2501/119* (2013.01); *C12N 2501/12* (2013.01); *C12N 2501/15* (2013.01); *C12N 2501/155* (2013.01); *C12N 2501/16* (2013.01); *C12N 2501/237* (2013.01); *C12N 2501/39* (2013.01); *C12N 2501/42* (2013.01); *C12N 2501/727* (2013.01); *C12N 2501/998* (2013.01); *C12N 2503/02* (2013.01); *C12N 2506/02* (2013.01); *C12Q 1/00* (2013.01)

(58) Field of Classification Search

CPC ........ A61K 35/407; C12N 5/067; C12N 5/00; C12N 2501/119; C12N 2501/12; C12N 2501/15; C12N 2501/155; C12N 2501/16; C12N 2501/237; C12N 2501/39; C12N 2501/42; C12N 2501/727; C12N 2501/998; C12N 2503/02; C12N 2506/02; C12Q 1/02; C12Q 1/00; G01N 33/50

See application file for complete search history.

(56) References Cited

U.S. PATENT DOCUMENTS

| | | | | |
|---|---|---|---|---|
| 2015/0166953 A1* | 6/2015 | Gupta | .................. | C12N 5/0672 424/553 |
| 2016/0002595 A1* | 1/2016 | Keller | ...................... | A61P 1/16 435/373 |
| 2017/0304369 A1* | 10/2017 | Ang | ..................... | C12N 5/0603 |

OTHER PUBLICATIONS

Hart et al. "A Comparison of Whole Genome Gene Expression Profiles of HepaRG Cells and HepG2 Cells to Primary Human Hepatocytes and Human Liver Tissues." Drug Metab Dispos. Jun. 2010;38(6):988-994. (Year: 2010).*

Pietrosi et al. "Phases I-II Matched Case-Control Study of Human Fetal Liver Cell Transplantation for Treatment of Chronic Liver Disease" Cell Transplant. 2015;24(8):1627-38 (Year: 2015).*

Richert et al "Gene expression in human hepatocytes in suspension after isolation is similar to the liver of origin, is not affected by hepatocyte cold storage and cryopreservation, but is strongly changed after hepatocyte plating." Drug Metab Dispos. May 2006;34(5):870-9. (Year: 2006).*

Agarwal, et al., Predicting effective microRNA target sites in mammalian mRNAs, 2015, Elife. 4. doi: 10.7554/eLife.05005, pp. 1-38.

Ambros, MicroRNAs and developmental timing, 2011, Curr Opin Genet Dev. 21(4): 511-7.

Backes, et al., A dictionary on microRNAs and their putative target pathways, 2010, Nucleic Acids Res. 38(13): 4476-86.

Buonato, et al., ERK1/2 blockade prevents epithelial-mesenchymal transition in lung cancer cells and promotes their sensitivity to EGFR inhibition, 2014, Cancer Res. 74(1): 309-19.

Cai, et al., Directed Differentiation of Human Embryonic Stem Cells into Functional Hepatic Cells, Hepatology (2007) 45: 1229-1239.

Chen, et al., Chemically defined conditions for human iPSC derivation and culture, 2011, Nat Methods. 8(5): 424-9.

Chen, et al., Mature hepatocytes exhibit unexpected plasticity by direct dedifferentiation into liver progenitor cells in culture, 2012, Hepatology. 55(2): 563-74.

D'Amour, et al., Efficient differentiation of human embryonic stem cells to definitive endoderm, Nat. Biotechnol., 23 (2005) pp. 1534-1541.

(Continued)

*Primary Examiner* — Titilayo Moloye

(74) *Attorney, Agent, or Firm* — McDonnell Boehnen Hulbert & Berghoff LLP

(57) ABSTRACT

This disclosure relates generally to new methods of maintaining the expression of hepatic genes in human hepatocytes and method for maintaining the functional hepatic enzyme activity of primary hepatocytes in culture. The disclosure also encompasses new methods of deriving a population of pure hepatocytes without selecting or sorting the cells from the cultured pluripotent cells.

11 Claims, 21 Drawing Sheets
(18 of 21 Drawing Sheet(s) Filed in Color)

(56) References Cited

OTHER PUBLICATIONS

Gerets, et al., Characterization of primary human hepatocytes, HepG2 cells, and HepaRG cells at the mRNA level and CYP activity in response to inducers and their predictivity for the detection of human hepatotoxins, 2012, Cell Biol Toxicol. 28(2):69-87.
Guo, et al., Stat3-coordinated Lin-28-let-7-HMGA2 and miR-200-ZEB1 circuits initiate and maintain oncostatin M-driven epithelial-mesenchymal transition, 2013, Oncogene, 32(45): 5272-82.
Hamilton, et al., Regulation of cell morphology and cytochrome P450 expression in human hepatocytes by extracellular matrix and cell-cell interactions, 2001, Cell Tissue Res. 306(1): 85-99.
Heo, et al., Lin28 mediates the terminal uridylation of let-7 precursor MicroRNA, 2008, Mol Cell. 32(2): 276-84.
Holtzinger, et al., New markers for tracking endoderm induction and hepatocyte differentiation from human pluripotent stem cells, 2015, Development. 142(24): 4253-65.
International Transporter Consortium, Membrane transporters in drug development, Nat Rev Drug Discov. Mar. 2010; 9(3): 215-236.
Kanehisa, et al., KEGG as a reference resource for gene and protein annotation, 2016, Nucleic Acids Res. 44(D1): D457-62.
Kanehisa, et al., KEGG: Kyoto encyclopedia of genes and genomes, (2000), Nucleic Acids Res. 28(1): 27-30.
Kuppusamy, et al., Let-7 family of microRNA is required for maturation and adult-like metabolism in stem cell-derived cardiomyocytes, 2015, Proc Natl Acad Sci U S A. 112(21): E2785-94.
Levy, et al., Long-term culture and expansion of primary human hepatocytes, 2015, Nat Biotechnol. 33(12): 1264-1271.
Loh, et al., Efficient endoderm induction from human pluripotent stem cells by logically directing signals controlling lineage bifurcations, 2014, Cell Stem Cell. 14(2): 237-52.
Pasquinelli, et al., Conservation of the sequence and temporal expression of let-7 heterochronic regulatory RNA, 2000, Nature. 408(6808): 86-9.
Pollack, et al., Oncostatin M-induced effects on EMT in human proximal tubular cells: differential role of ERK signaling, 2007, Am J Physiol Renal Physiol. 293(5): F1714-26.
Reinhart, et al., The 21-nucleotide let-7 RNA regulates developmental timing in Caenorhabditis elegans, 2000, Nature, 403(6772): 901-6.
Schulze, et al., Hepatocyte Polarization Is Essential for the Productive Entry of the Hepatitis B Virus, 2012, Hepatology 2012;55:373-383.
Sengupta, et al., Aggregate culture of human embryonic stem cell-derived hepatocytes in suspension are an improved in vitro model for drug metabolism and toxicity testing, 2014, Toxicol Sci. 140(1): 236-45.
Shlomai, et al., Modeling host interactions with hepatitis B virus using primary and induced pluripotent stem cell-derived hepatocellular systems, PNAS, Aug. 19, 2014, vol. 111, No. 33, 12193-12198.
Smith, et al., Snail promotes epithelial mesenchymal transition in breast cancer cells in part via activation of nuclear ERK2, 2014, PLoS One. 9(8): e104987.
Soldatow, et al., In vitro models for liver toxicity testing, (2013). VY, Lecluyse EL, Griffith LG, Rusyn. Toxicol Res (Camb). 2(1): 23-39.
Tennessen, et al., Developmental timing: let-7 function conserved through evolution, 2008, Curr Biol. 18(16): R707-8.
Wang, et al., Notch is the key factor in the process of fetal liver stem/progenitor cells differentiation into hepatocytes, 2012, Dev Growth Differ. 54(5): 605-17.
Yu, et al., Induced pluripotent stem cell lines derived from human somatic cells, 2007, Science. 318(5858): 1917-20.
Donato et al., "Cell lines: a tool for in vitro drug metabolism studies," Curr Drug Metab. 9(1):1-11 (Jan. 2008).
Huang et al., "Bioinformatics enrichment tools: paths toward the comprehensive functional analysis of large gene ists," Nucleic Acids Res. 37(1):1-13 (Jan. 2009). Epub Nov. 2008.
Jiang et al., "Drug-metabolizing enzyme, transporter, and nuclear receptor genetically modified mouse models," Drug Metab Rev. 43(1):27-40 (Feb. 2011). Epub Sep. 2010.
Knowles et al., "Human hepatocellular carcinoma cell lines secrete the major plasma proteins and hepatitis B surface antigen," Science 209(4455):497-9 (Jul. 1980).
Martignoni et al., "Species differences between mouse, rat, dog, monkey and human GYP-mediated drug metabolism, inhibition and induction," Expert Opin Drug Metab Toxicol. 2(6):875-94 (Dec. 2006).
Mitchell et al., "The InterPro protein families database: the classification resource after 15 years," Nucleic Acids Res. 43:D213-21 (Jan. 2015). Epub Nov. 2014.
Schwartz et al., "Modeling hepatitis C virus infection using human induced pluripotent stem cells," Proc Nall Acad Sci USA 109(7):2544-8 (Feb. 2012). Epub Jan. 2012.
Williams, "Application of hepatocyte-like cells to enhance hepatic safety risk assessment in drug discovery," Philos Trans R Soc Lond B Biol Sci. 373(1750) pp. 1-8 (Jul. 2018).
Gieseck et al. "Generation of Hepatocytes from Pluripotent Stem Cells for Drug Screening and Developmental Modeling," Methods Mol Biol 1250:123-42 (2015).
Pei et al. "Regulation of hepatitis C virus replication and gene expression by the MAPK-ERK pathway," Virol Sin. 27(5) 278-85 (Oct. 2012). Epub Sep. 2021.
Henklova et al. "SB203580, a pharmacological inhibitor of p38 MAP kinase transduction pathway activates ERK and JNK MAP kinases in primary cultures of human hepatocytes," Eur J Pharmacol. 593(1-3): 16-23 (Sep. 2008). Epub Jul. 2008.
Breunig et al., "BRaf and MEK Inhibitors Differentially Regulate Cell Fate and Microenvironment in Human Hepatocellular Carcinoma," Clin Cancer Res 20(9):2410-23 (May 2014).

* cited by examiner

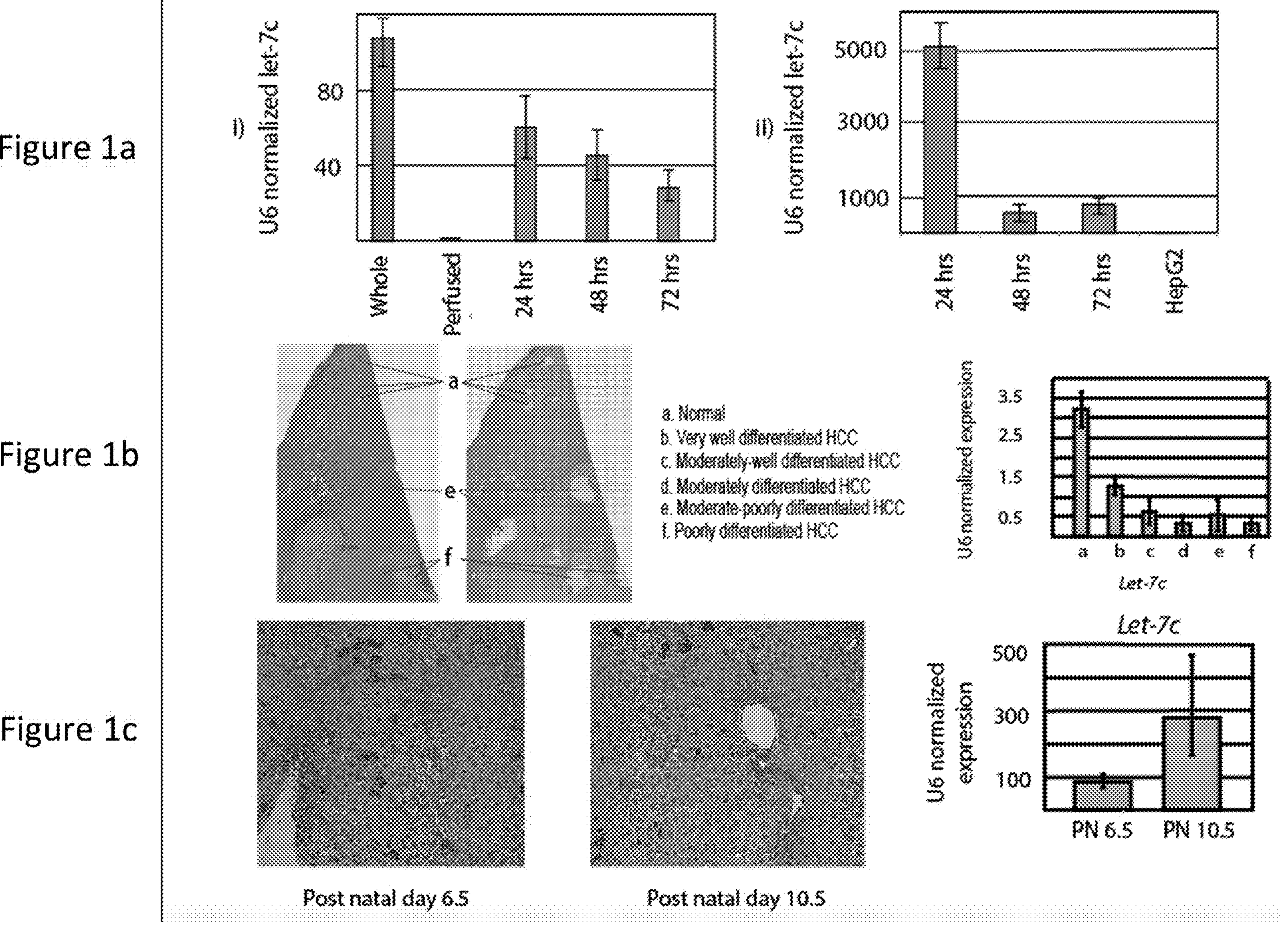

Figure 1a
i)
U6 normalized let-7c
80
40
Whole
Perfused
24 hrs
48 hrs
72 hrs
ii)
U6 normalized let-7c
5000
3000
1000
24 hrs
48 hrs
72 hrs
HepG2
Figure 1b
a
e
f
a. Normal
b. Very well differentiated HCC
c. Moderately-well differentiated HCC
d. Moderately differentiated HCC
e. Moderate-poorly differentiated HCC
f. Poorly differentiated HCC
U6 normalized expression
3.5
2.5
1.5
0.5
a b c d e f
Let-7c
Figure 1c
Post natal day 6.5
Post natal day 10.5
Let-7c
U6 normalized expression
500
300
100
PN 6.5
PN 10.5

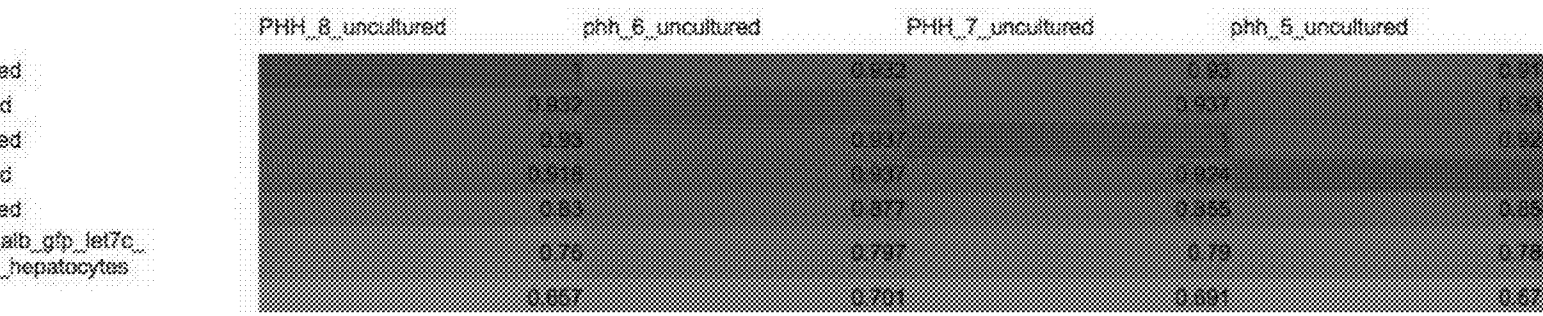

| | PHH_8_uncultured | phh_6_uncultured | PHH_7_uncultured | phh_5_uncultured |
|---|---|---|---|---|
| PHH_8_uncultured | 1 | 0.932 | 0.93 | 0.916 |
| phh_6_uncultured | 0.932 | 1 | 0.937 | 0.937 |
| PHH_7_uncultured | 0.93 | 0.937 | 1 | 0.924 |
| phh_5_uncultured | 0.916 | 0.937 | 0.924 | 1 |
| PHH_9_uncultured | 0.83 | 0.877 | 0.865 | 0.854 |
| alb_positive_h9_alb_gfp_let7c_clone_2_derived_hepatocytes | 0.75 | 0.797 | 0.79 | 0.784 |
| Hep_G2_ND | 0.657 | 0.701 | 0.691 | 0.677 |

Figure 9a

For group 2, "liver genes", spearman correlations:

| | PHH_8_uncultured | PHH_7_uncultured | phh_5_uncultured | phh_6_uncultured |
|---|---|---|---|---|
| PHH_8_uncultured | 1 | 0.982 | 0.975 | 0.973 |
| PHH_7_uncultured | 0.982 | 1 | 0.974 | 0.971 |
| phh_5_uncultured | 0.975 | 0.974 | 1 | 0.972 |
| phh_6_uncultured | 0.973 | 0.971 | 0.972 | 1 |
| PHH_9_uncultured | 0.86 | 0.856 | 0.867 | 0.858 |
| alb_positive_h9_alb_gfp_let7c_clone_2_derived_hepatocytes | 0.758 | 0.758 | 0.775 | 0.747 |
| Hep_G2_ND | 0.377 | 0.358 | 0.383 | 0.377 |

Figure 10A:
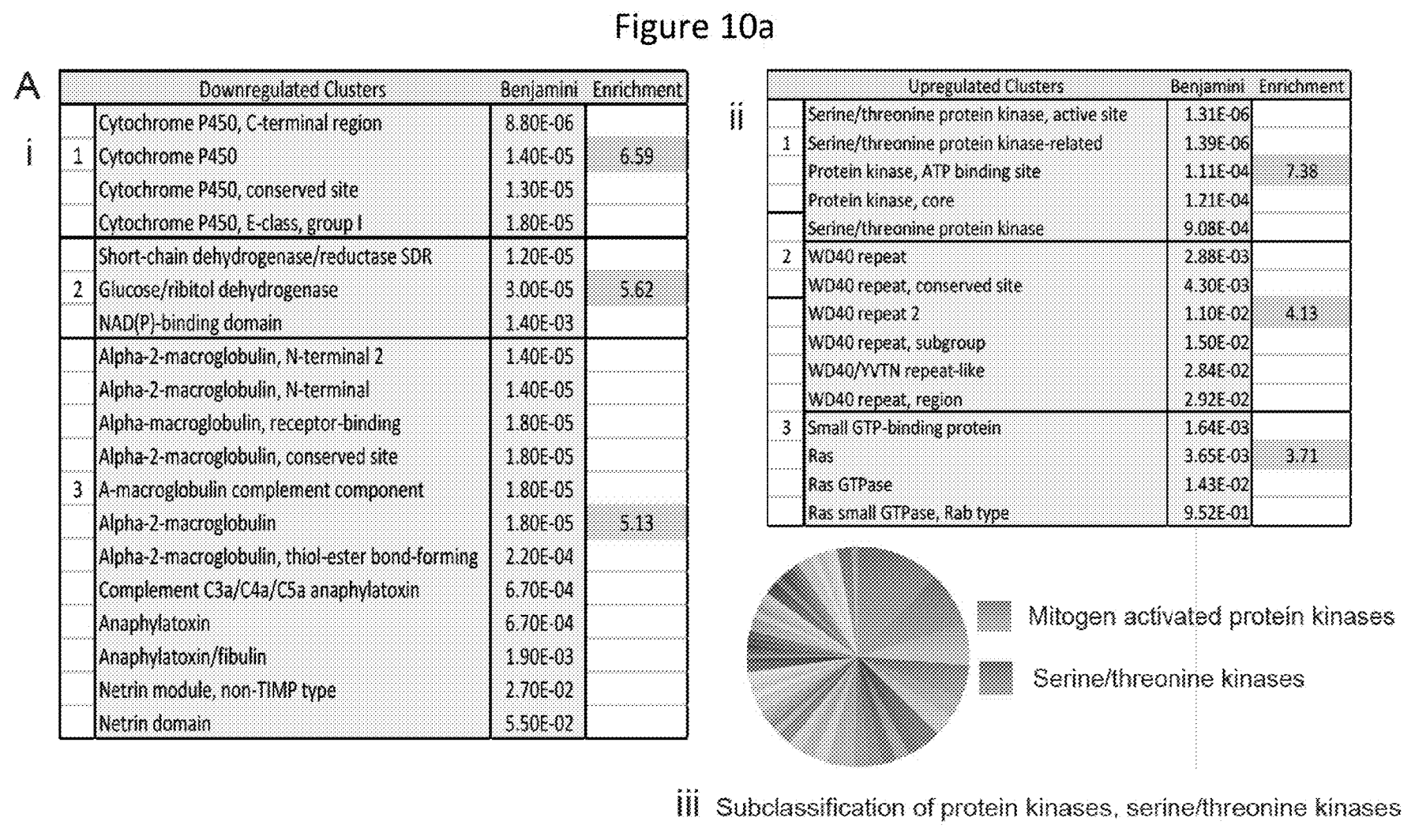

| | Downregulated Clusters | Benjamini | Enrichment |
|---|---|---|---|
| | Cytochrome P450, C-terminal region | 8.80E-06 | |
| 1 | Cytochrome P450 | 1.40E-05 | 6.59 |
| | Cytochrome P450, conserved site | 1.30E-05 | |
| | Cytochrome P450, E-class, group I | 1.80E-05 | |
| | Short-chain dehydrogenase/reductase SDR | 1.20E-05 | |
| 2 | Glucose/ribitol dehydrogenase | 3.00E-05 | 5.62 |
| | NAD(P)-binding domain | 1.40E-03 | |
| | Alpha-2-macroglobulin, N-terminal 2 | 1.40E-05 | |
| | Alpha-2-macroglobulin, N-terminal | 1.40E-05 | |
| | Alpha-macroglobulin, receptor-binding | 1.80E-05 | |
| | Alpha-2-macroglobulin, conserved site | 1.80E-05 | |
| 3 | A-macroglobulin complement component | 1.80E-05 | |
| | Alpha-2-macroglobulin | 1.80E-05 | 5.13 |
| | Alpha-2-macroglobulin, thiol-ester bond-forming | 2.20E-04 | |
| | Complement C3a/C4a/C5a anaphylatoxin | 6.70E-04 | |
| | Anaphylatoxin | 6.70E-04 | |
| | Anaphylatoxin/fibulin | 1.90E-03 | |
| | Netrin module, non-TIMP type | 2.70E-02 | |
| | Netrin domain | 5.50E-02 | |

ii

| | Upregulated Clusters | Benjamini | Enrichment |
|---|---|---|---|
| | Serine/threonine protein kinase, active site | 1.31E-06 | |
| 1 | Serine/threonine protein kinase-related | 1.39E-06 | |
| | Protein kinase, ATP binding site | 1.11E-04 | 7.38 |
| | Protein kinase, core | 1.21E-04 | |
| | Serine/threonine protein kinase | 9.08E-04 | |
| 2 | WD40 repeat | 2.88E-03 | |
| | WD40 repeat, conserved site | 4.30E-03 | |
| | WD40 repeat 2 | 1.10E-02 | 4.13 |
| | WD40 repeat, subgroup | 1.50E-02 | |
| | WD40/YVTN repeat-like | 2.84E-02 | |
| | WD40 repeat, region | 2.92E-02 | |
| 3 | Small GTP-binding protein | 1.64E-03 | |
| | Ras | 3.65E-03 | 3.71 |
| | Ras GTPase | 1.43E-02 | |
| | Ras small GTPase, Rab type | 9.52E-01 | |

iii Subclassification of protein kinases, serine/threonine kinases

GENERATION OF UNIFORM HEPATOCYTES FROM HUMAN EMBRYONIC STEM CELLS BY INHIBITING TGF-BETA AND METHODS OF MAINTAINING HEPATIC CULTURES

CROSS-REFERENCE TO RELATED APPLICATIONS

This application is a divisional of U.S. application Ser. No. 15/650,595, filed on Jul. 14, 2017, which claims priority to U.S. Provisional Application Nos. 62/362,385 filed on Jul. 14, 2016 and 62/531,424 filed on Jul. 12, 2017, the contents of each of which are incorporated by reference in their entireties.

STATEMENT REGARDING FEDERALLY SPONSORED RESEARCH

This invention was made with government support under RD-83573701-0 awarded by the Environmental Protection Agency. The government has certain rights in the invention.

BACKGROUND OF THE INVENTION

In vitro liver models provide an essential tool for the study of liver disease, hepatotoxicity, hepatotropic viruses, and drug and antiviral development; however, the lack of availability, significant donor-to-donor variability, and rapid dedifferentiation of primary human hepatocytes (PHHs) in culture severely hinders their use in research. The problem being that PHHs lose their mature phenotype shortly after isolation or removal from their in vivo environment (1). Attempts at maintaining long-term maturity of PHHs in culture, or to mature fetal hepatic cells, have shown limited success. Culture systems designed to mimic the hepatocyte microenvironment (sandwich and aggregate cultures) and co-culture methods with other non-parenchymal liver cells have not been able to significantly enhance the viability of cultured PHHs or mature fetal hepatocytes (ibid).

Due to these challenges, fetal hepatic cell lines such as HepG2 have traditionally been used for drug testing (ibid). While oncogenically transformed hepatic cell lines such as HepG2 have the advantage of being abundant, expandable, and easy to culture, their use in in vitro liver modeling is limited as they are fetal in nature, refractory to infection by hepatotropic viruses, and a poor metabolizer of xenobiotics due to a lack of, or low levels of, many phase I and II enzymes and drug transporters (2).

Further, populations of hepatocytes derived from human embryonic stem (ES) cells and induced pluripotent stem (iPS) cells contain other developmentally close cell lineages hindering their use in drug development and other studies. Poor metabolic activity and toxicity response of ES-derived hepatocytes could be attributed to not only their immature nature, but also to the presence of non-hepatic cells in the population generated during differentiation. Conventional profiling of selected metabolic genes may be misleading as to the identity of differentiated cells because some developmentally close cell types such as gut, involved in first pass metabolism, also express a number of metabolism-associated genes and may be misconstrued as hepatocytes. Flow cytometric analysis of hepatocyte specific surface antigens and multiple hepatic markers is necessary for faithful identification of differentiated cells.

Thus, there is both the need in the art for methods of maintaining or inducing certain levels of expression of genes on hepatocytes to maintain their functionality and also methods of obtaining pure populations hepatocytes during differentiation and culturing from pluripotent cells.

SUMMARY OF THE INVENTION

This disclosure relates generally to new methods of maintaining the expression of one or more genes found in fresh primary hepatocytes in cultured human hepatocytes. Additionally, the disclosure is related to new methods of deriving a population of pure hepatocytes without selecting or sorting the cells from pluripotent cells.

In one aspect, the disclosure provides a method of expressing or inducing expression in a human hepatocyte of one or more gene selected from the group consisting of Bile Acid-CoA:Amino Acid N-Acyltransferase (BAAT), Solute Carrier Organic Anion Transporter Family Member 1B1 (SLCO1B1), Cytochrome P450 Family 1 Subfamily B Member 1 (CYP1B1), Cytochrome P450 Family 2 Subfamily C Member 18 (CYP2C18), UDP Glucuronosyltransferase Family 1 Member A6 (UGT1A6), UDP-glucuronosyltransferase 1-9 (UGT1A9), and Cluster of Differentiation 81 (CD81). The method comprises the steps of culturing the human hepatocyte with at least one inhibitor of mitogen activating protein kinase (MAPK), wherein the cultured human hepatocyte expresses the one or more gene at a minimum level, wherein the minimum level of each gene is at least 70% the expression level of each gene in fresh primary hepatocytes.

In some aspects, the disclosure provides an ex vivo hepatocyte culture comprising the cultured hepatocytes produced by the method and at least one inhibitor of MAPK, wherein the cultured human hepatocytes maintain expression levels of one or more gene selected from the group consisting of BAAT, SLCO1B1, CYP1B1, CYP2C18, UGT1A6, UGT1A9, and CD81 at a minimum level for at least 24 hours in culture, preferably at least 72 hours in culture, wherein the minimum level of the one or more gene is at least 70% the expression level of each gene in fresh primary hepatocytes.

In a further aspect, the disclosure provides a method of culturing hepatitis virus in cell culture, the method comprising the steps of: culturing a hepatitis virus and one or more hepatocyte cell expressing BAAT, SLCO1B1, CYP1B1, CYP2C18 UGT1A6, UGT1A9, and CD81 at a minimum level with at least one inhibitor of MAPK wherein the hepatitis virus is able to replicate within the cultured hepatocyte cell.

In another embodiment, the disclosure provides a method of culturing an essentially pure population of hepatocytes expressing ASGR1 and albumin from human pluripotent stem cells, the method comprising the steps of culturing the pluripotent stem cells in a defined medium comprising at least one inhibitor of transforming growth factor (TGF)-β and at least one inhibitor of NOTCH, wherein at least 95% of the cells in the culture express ASGRI and albumin.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1*a* depicts bar graphs demonstrating Let-7c expression is associated with hepatocyte differentiation as shown by decrease in Let-7c levels in dedifferentiating primary hepatocytes in culture. i) U6 normalized let-7c expression in primary mouse hepatocytes decreases after isolation from the liver. It is partially regained in confluent culture and goes down when cells dedifferentiate over time. ii) Let-7c expression (U6 normalized) also decreases in primary human hepatocytes (mixture from 4 donors) over 72 hours. HepG2, a fetal hepatic cell line shows very low levels of let-7c expression.

FIG. 1*b* depicts representative images demonstrating that human liver cancer or hepatocellular carcinoma (HCC) arises as a well differentiated tumor and gradually dedifferentiates with disease progression. i) A section of a human liver containing HCC of various differentiation grades is shown. The picture on the right shows those areas after harvesting by laser microdissection. ii) Bar graph demonstrates that Let-7c expression is gradually lost with progressive HCC dedifferentiation.

FIG. 1*c* provides representative images showing Let-7c is associated with mouse liver development in mouse liver sections. i) Sections of mouse liver on postnatal day 6.5 and 10.5 showing that the majority of cells are hepatocytes. ii) Let-7c levels increase with maturation of the liver. All microRNA measurements were done by qPCR and normalized to U6 levels. Levels are expressed in relative quantity (RQ) with error bars representing RQ minimum and RQ maximum derived from standard error.

FIG. 2*a*. Let-7c transduction in HepG2 upregulates drug metabolism and reduces cell proliferation. Let-7c transduction in primary human hepatocytes leads to 5-fold increased expression of the microRNA at 72 hours in culture compared to scrambled control transduction at the same time. MicroRNA expression was measured by qPCR and normalized to U6 snoRNA. Levels are expressed in RQ (relative quantity) with error bars representing RQ minimum and RQ maximum derived from standard error FIG. 2*b*. U0126 upregulates drug metabolism by CYP3A4 and CYP2C9 in HepG2 cells.

FIG. 2*c*. MAPK inhibition leads to reduced viability of HepG2. Cells treated with both U0126 and PD0325901 for 72 hours show increased cell death and growth arrest compared to vehicle control treated cells.

FIGS. 9*a*-9*b*. FIGS. 9*a* and 9*b* shows the correlation by their gene expression profiles (measured by RNA-Seq) between let-7c expressing ES-derived hepatocytes (alb_positive H9_alb_GFP-let7c_clone2_derived hepatocytes) and mature uncultured adult primary human hepatocytes (PHH 5 through 9) along with control HepG2 cells by whole transcriptome (9*a*) and liver specific genes (9*b*). These figures demonstrate that let-7c expressing ES-derived hepatocytes have great similarity to adult primary hepatocytes (correlation coefficient of >0.75) while HepG2s have lower score, being fetal in nature.

FIG. 9*c* is a bar graph depicting the levels of let7c as measured by QPCR in hepatocytes derived from the two clones, 9-ALB-GFP/AFP-Tomato (labeled H9 ALB hepatocyte) and H9-ALB-GFP-let7c.

FIG. 10*a*. Classification of genes differentially expressed in primary human hepatocytes (PHHs) by their protein classes in UNIPROT through DAVID, before and after culturing for 24 hours. i) and ii) shows the three most statistically enriched clusters of downregulated and upregulated genes respectively. iii) MAP kinases comprised the largest group of genes within the upregulated protein and serine/threonine kinases.

DETAILED DESCRIPTION OF THE INVENTION

Figure 3:
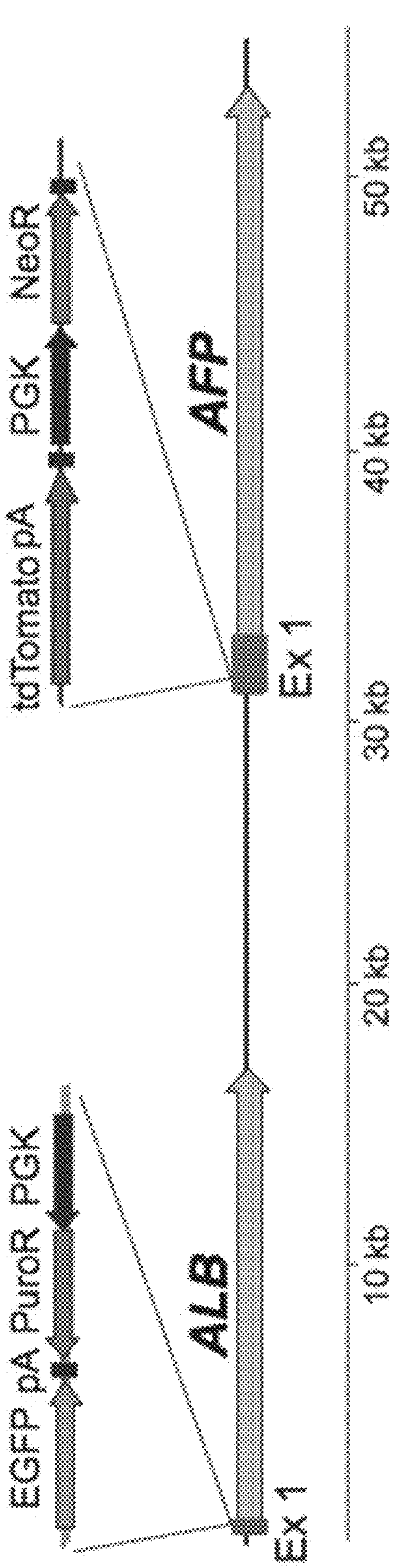
FIG. 3. Schematic of the construct used to generate the dual ALB-GFP/tdTomato-AFP reporter cell line.

This disclosure relates generally to new methods of maintaining the expression of mature hepatic genes in human hepatocytes and method for maintaining the functional hepatic enzyme activity of primary hepatocytes in culture. The disclosure also encompasses new methods of deriving a population of pure hepatocytes without selecting or sorting the cells from the cultured pluripotent cells.

Method of Maintaining Maturation of Hepatocytes in Culture or Maturing Immature Hepatocytes Cultured primary human hepatocytes (PHHs) are an indispensable tool for drug development and toxicity testing, but lack of availability and short viability in vitro has hindered their use. This is primarily due to the fact that they dedifferentiate in culture and lose their mature phenotype (i.e. expression of mature hepatic [drug metabolism and other adult liver function-associated] genes as compared with freshly isolated primary hepatocytes). Further, immature hepatocytes, such as fetal hepatocytes, do not express mature hepatic genes or provide the enzymatic functions as compared with freshly isolated primary hepatocytes. Liver cancer cell lines also de-differentiate in culture, losing their fresh primary hepatocyte phenotype. Thus, there is a need to maintain expression of hepatic genes at high enough expression level to maintain the phenotype and functionality as in fresh primary hepatocytes.

The present disclosure demonstrates that inhibitors of MAPK pathway when added to human hepatocytes in cell culture are able to maintain or induce minimum expression of one or more genes selected from Bile Acid-CoA:Amino Acid N-Acyltransferase (BAAT), Solute Carrier Organic Anion Transporter Family Member 1B1 (SLCO1B1), Cytochrome P450 Family 1 Subfamily B Member 1 (CYP1B1), Cytochrome P450 Family 2 Subfamily C Member 18 (CYP2C18), UDP Glucuronosyltransferase Family 1 Member A6 (UGT1A6), UDP-glucuronosyltransferase 1-9 (UGT1A9), and Cluster of Differentiation 81 (CD81) in the cultured hepatocytes. The minimum expression level of each gene is at least 70% the level of the same gene in a fresh primary hepatocyte. These cultured hepatocyte cells maintain sufficient levels of the one or more of the gene BAAT, SLCO1B1, CYP1B1, CYP2C18, UGT1A6, UGT1A9, and CD81 at a minimum level as to be functional for use for liver function studies, toxicity and metabolic testing. Further, these cells are able to be infected by and propagate hepatitis virus.

The hepatocytes of interest in the present disclosure are the cultured hepatocytes produced by the disclosed methods of culturing a human hepatocyte with at least one inhibitor of MAPK. These hepatocytes are cells that express one or more of the gene BAAT, SLCO1B1, CYP1B1, CYP2C18, UGT1A6, UGT1A9, and CD81 at a minimum level when compared with the level of the same gene in fresh primary hepatocytes. These cells are able to perform functions of primary hepatocytes, for example, at least one liver metabolic activity.

The term "primary hepatocyte" refers to a hepatocyte cell obtained by isolating cells obtained from liver tissue and culturing ex vivo. Primary hepatocytes de-differentiate in culture in a very short time and do not grow in culture without additional manipulation.

For purposes herein, the term "fresh primary hepatocytes" or "uncultured primary hepatocytes" refers to commercially available cryopreserved hepatocytes that were not thawed or cultured once received.

The disclosure provides a method of maintaining or inducing the expression of one or more gene, alternatively two or more genes, alternatively three or more genes, alternatively four or more genes, alternatively five or more genes, alternatively six or more genes selected from the group consisting of BAAT, SLCO1B1, CYP1B1, CYP2C18, UGT1A6, UGT1A9, and CD81 in a hepatocyte at a minimum level by culturing the hepatocyte with at least one inhibitor of mitogen activating protein kinase (MAPK). In one embodiment, the disclosure provides a method of maintaining or inducing expression of BAAT, SLCO1B1, CYP1B1, CYP2C18, UGT1A6, UGT1A9, and CD81 each at a minimum level by culturing the hepatocyte with at least one inhibitor of MAPK.

Inhibitors of MAPK are known in the art and include, but are not limited to, for example, inhibitors of p38, mitogen activated and extracellular regulated kinase (MEK)1 and MEK2 protein kinases, for example, U0126 (a dual MEK1 & MEK2 inhibitor), PD098059 (a MEK1 inhibitor), and SB203580 (a p38 MAP kinase inhibitor), AZD6244 (MEK1 inhibitor), Trametinib (GSK1120212, MEK1/2 inhibitor) TAK 715, SB203580, SB202190, PD0325901, PD184352, SB239063, SB706504, and combinations thereof. In a preferred embodiment, the at least one MAPK inhibitor is U0126. In another preferred embodiment, the MAPK inhibitor is PD09059. In some embodiments the at least one MAPK inhibitor is a combination of U0126 and PD09059.

Suitable concentrations of MAPK inhibitors used in the present methods and kits include, but are not limited to, about 10 nm to about 10 mM, alternatively about 10 nm to about 2 mM, alternatively about 10 nm to about 1 mM, alternatively from about 10 nm to about 500 μM, alternatively from about 100 nm to about 2 mM, alternatively from about 100 nm to about 1000 μM, alternatively from about 1 μM to about 200 μM, alternatively about 1 μM to about 100 μM of the MAPK inhibitor. For example, in one embodiment, the concentration of MAPK is from about 5 μM to about 150 μM, alternatively from about 5 μM to about 50 μM, alternatively about 5 μM to about 10 μM. In a preferred embodiment, the MAPK inhibitor is used in an amount of about 10 μM.

In some aspects, the cultured hepatocytes further express at least one mature hepatic gene. Suitable mature hepatic genes can be found, for example, in Table 4 of the examples. In some embodiments, the at least one mature hepatic gene is selected from the group consisting of CYP1A2, CYP2C9, CYP2D6, CYP2E1, CYP3A4, UGT1A1, SLCO1B3 and ALB at a minimum expression level, and wherein the minimum expression level is at least 70% of the expression level of the at least one mature hepatic gene in fresh primary hepatocytes as measured by RNA levels or protein levels within the cells. Other suitable mature hepatic genes can be found in, for example, Table 3 or 5.

The minimum expression level is a level of the gene that is expressed as compared to the expression level of the same gene in fresh primary hepatocytes. In some embodiments, the minimum expression level is at least 70% as compared with the expression level in fresh primary hepatocytes. In some embodiments, it is at least 75% as compared with the expression level in fresh primary hepatocytes. In some embodiments, it is at least 80%, alternatively at least 85%, alternatively at least 90% as compared with the expression level in fresh primary hepatocytes. In some embodiments, the minimal expression level is at least 95%, alternatively at least 100% as compared with the expression level in fresh primary hepatocytes. In some alternatively embodiments, the expression level of the gene in the cultured cells of the present invention is greater than the expression level of that same gene in fresh primary hepatocytes, for example, may be at least 110%, alternatively at least 120%, alternatively at least 130%, alternatively at least 140%, alternatively at least 150%, alternatively at least 160%, alternatively at least 180%, alternatively at least 200% as compared with the expression levels of the same gene in fresh primary hepatocytes.

The expression levels can suitably be measured by quantitating RNA levels within the cells. In an alternate embodiment, the expression levels can be measured by quantitating the protein levels within the cells.

In some embodiments, the minimal expression level of selected hepatic genes is maintained for at least 72 hours, in culture. In some embodiments, the minimal expression level is maintained for at least four (4) days, alternatively at least five (5) days, alternatively at least six (6) days, alternatively at least one week in cell culture. In some embodiments, the minimum expression levels are maintained for at least one week, at least ten (10) days, at least two weeks or more in cell culture.

The methods of culturing hepatocytes with at least one MAPK inhibitor also inhibit upregulation of the fetal marker AFP in hepatocytes (for example inhibits upregulation in primary hepatocyte cells), and in some instances, results in the downregulation of AFP in immature hepatocytes. In both cases, the hepatocytes that result maintain a level of AFP within five fold of the level of AFP found in fresh primary hepatocytes, whether it is maintaining the low level expression of differentiated hepatocytes or the downregulation of expression in immature hepatocytes.

In some further embodiments, the disclosure provides an ex vivo hepatocyte cell culture comprising one or more human hepatocytes produced by the method described above. The ex vivo hepatocyte culture comprises hepatocytes which maintain expression levels of one or more of BAAT, SLCO1B1, CYP1B1, CYP2C18, UGT1A6, UGT1A9, and CD81 at a minimum level, wherein the minimum level is at least 70% of the expression level of the gene in fresh primary hepatocytes. In some embodiments, the hepatocytes maintain minimum expression levels of one or more of BAAT, SLCO1B1, CYP1B1, CYP2C18, UGT1A6, UGT1A9, and CD81 for at least 72 hours in the culture. In some embodiments, the hepatic cells maintain expression for at least five (5) days in culture.

Suitable culture conditions for culturing hepatocytes are known in the art. A suitable medium is any medium that allows for the growth and expansion of hepatocytes in culture, as long as the medium does not contain antagonists of MAPK inhibitors.

In some embodiments, the human hepatocyte is a primary hepatocyte.

In some embodiments, the human hepatocytes are immature hepatocytes. In some embodiments, the immature hepatocyte is a fetal hepatocyte, a cultured hepatic cancer cell line or an immortalized primary hepatic cell line. Suitable hepatic cancer cell lines, include, but are not limited to, for example, HepG2 cell line, Huh7, Hep3B, PLC/PRF/5, and Huh6 among others. Suitable hepatic cell lines are available in the art, for example from American Type Culture Collection (ATCC).

As used herein, the term "fetal hepatocyte" refers to a putative hepatocyte that is differentiated from human pluripotent cells, such as hES cells or hiPS cells, and exhibits a morphology similar to that of primary hepatocytes, that secretes albumin and expresses one or more markers associated with liver cells, but not CYP2C9, CYP2D6, CYP2E1, CYP3A4, UGT1A6 and UGT1A9 at levels equal to fresh uncultured primary hepatocytes and which cannot metabolize drugs through the above enzymes at rate equal to that of fresh uncultured primary hepatocytes.

In some embodiments, the method of maturing immature hepatocytes comprises culturing the immature hepatocytes with at least one MAPK inhibitor, wherein the immature hepatocytes after culturing have at least two-fold reduction in the expression of an alpha-fetoprotein (AFP) and express one or more genes selected from the group consisting of BAAT, SLCO1B1, CYP1B1, CYP2C18, UGT1A6, UGT1A9, and CD81 at a minimum level of at least 70% the level of that gene found in fresh primary hepatocytes.

In some embodiments, the immature hepatocytes after culturing have at least 2.5 fold, alternatively at least 4 fold reduction in the expression of AFP. In alternative embodiments, the method of maturing immature hepatocytes comprises culturing the immature hepatocytes with at least one MAPK inhibitor, wherein the immature hepatocytes after culturing have at least a 50% reduction in the expression of AFP, alternatively at least a 60% reduction in the expression of AFP, alternatively at least a 75% reduction in the expression of AFP. In further embodiments, the method results in at least 80% reduction in the expression of AFP, alternatively at least 85% reduction in the expression of AFP within the immature cells.

The expression levels of the genes described herein can be measured by quantitative methods known in the art, and include, for example, quantitative real time PCR (QRT PCR).

In another embodiment, the disclosure provides a composition comprising cultured hepatocyte cells derived from the method described above and at least one inhibitor of MAPK, wherein the hepatocyte cells maintain their expression of one or more of BAAT, SLCO1B1, CYP1B1, CYP2C18, UGT1A6, UGT1A9, and CD81 for at least 72 hours in culture.

There is a need for cell cultures that can replicate hepatitis virus, both for the growth of virus for vaccines and for the study of hepatitis liver infection and suitable treatments thereof. In some embodiments, the present disclosure provides a hepatic cell culture able to replicate hepatitis virus within the culture. In some aspects, the disclosure also encompasses an in vitro method for supporting the replication of a hepatitis virus in culture. The method includes the step of exposing one or more hepatocytes prepared according to the methods described herein to a hepatitis virus. The hepatitis virus replicates within the one or more hepatocytes. In certain embodiments, the hepatitis virus is hepatitis B virus (HBV) or hepatitis C virus (HCV). In some embodiments, the hepatitis virus is selected from the group consisting of Hepatitis A (HAV), Hepatitis B (HBV), Hepatitis C (HCV), Hepatitis D (HDV), and Hepatitis E (HEV).

In some embodiments, the present disclosure provides a hepatocyte culture able to replicate at least one hepatitis virus within at least one hepatocyte for at least 72 hours. In other embodiments, the virus is able to replicate within the hepatocyte culture for at least four days, alternatively at least five days, alternatively for at least a week within the culture.

The disclosure also provides a method of culturing hepatitis virus in cell culture, the method comprising the steps of culturing a hepatitis virus and one or more hepatocyte cell obtained by the methods of the present disclosure with at least one inhibitor of MAP kinase (MAPK), wherein the hepatitis virus is able to replicate within the one or more hepatocyte cell.

In some embodiments, the methods provide one or more hepatocyte that express the HBV receptor, SLC10A1 and/or the HCV receptor, CD81, more preferably express both the HBV and HCV receptors at a level of at least 70% the expression level found in fresh primary hepatocytes (e.g., at least 70%, at least 75%, at least 80%, at least 85%, at least 90%, etc).

In one embodiment, a hepatic cancer cell line, e.g. Hep G2, is cultured with at least one MAPK inhibitor, wherein the hepatic cancer cell line expresses SLC10A1 and CD81 at a level of at least 70% the expression level found in fresh primary hepatocytes (e.g., at least 70%, at least 75%, at least 80%, at least 85%, at least 90%, etc). These cells are able to allow replication of HBV and/or HCV within the cells, providing a cost effective cell source for replicating hepatitis virus, studying HBV/HCV infection and also for studying the mechanism of viral induced liver disease.

The present inventors using a compound screen have identified Stauprimide, a c-myc inhibitor, as another compound that can be used in the methods described above for MAPK inhibitor for the maturation and maintaining of mature hepatocytes. The present disclosure thus additionally provides methods of maintaining maturation of hepatocytes in culture or maturing immature hepatocytes using a c-myc inhibitor, Stauprimide. The method of culturing hepatocytes with at least one c-myc inhibitor, preferably Stauprimide, increases expression of albumin and also inhibits upregulation of the fetal marker AFP in hepatocytes (for example inhibits upregulation in primary hepatocyte cells), and in some instances, results in the downregulation of AFP in immature hepatocytes. In one embodiment, the disclosure provides a method of expressing or inducing expression in a human hepatocyte of one or more mature hepatocyte genes by culturing the hepatocytes with a c-myc inhibitor, preferably Stauprimide. In some embodiments, the one or more mature hepatocyte gene is selected from the group consisting of UGT1A9, UGT1A6, CYP2C9, CYP1A1, HNF4A, ADH4, BAAT, SERPINC1, SERPINA1, and combinations thereof. In another embodiment, the one or more gene is selected from the group consisting of BAAT, SLCO1B1, CYP1B1, CYP2C18, UGT1A6, UGT1A9, and CD81. The method comprises the steps of culturing the human hepatocyte with at least one inhibitor c-myc inhibitor, e.g. Stauprimide, wherein the cultured human hepatocyte expresses the one or more gene at a minimum level, wherein the minimum level of each gene is at least 70% the expression level of each gene in fresh primary hepatocytes.

In some embodiments, the disclosure provides an ex vivo hepatocyte culture comprising the cultured mature human hepatocytes and Stauprimide, wherein the cultured mature human hepatocytes maintain expression levels of one or more mature hepatocyte gene at a minimum level for at least 24 hours in culture, preferably at least 72 hours in culture, wherein the minimum level of the one or more gene is at least 70% the expression level of each gene in fresh primary hepatocytes.

In another embodiment, the disclosure provides a method of maintaining or inducing the expression of one or more gene, alternatively two or more genes, alternatively three or more genes, alternatively four or more genes, alternatively five or more genes, alternatively six or more genes selected from the group consisting of BAAT, SLCO1B1, CYP1B1, CYP2C18, UGT1A6, UGT1A9, ALB, UGT1A6, CYP2C9, CYP1A1, HNF4A, ADH4, SERPINC1, SERPINA1, and CD81 in a hepatocyte at a minimum level of at least 70% the level of that gene found in fresh primary hepatocytes by culturing the hepatocyte with at least one inhibitor of c-myc, preferably Stauprimide. In one embodiment, the disclosure provides a method of maintaining or inducing expression of BAAT, SLCO1B1, CYP1B1, CYP2C18, UGT1A6, UGT1A9, and CD81 each at a minimum level by culturing the hepatocyte with at least one inhibitor of c-myc, preferably Stauprimide.

Suitable concentrations of Stauprimide for use in the methods and kits of the described herein include, but are not limited to, about 10 nm to about 10 mM, alternatively about 10 nm to about 2 mM, alternatively from about 10 nm to about 1 mM, alternatively from about 10 nm to about 500 μM, alternatively from about 100 nm to about 200 μM, alternatively from about 100 nm to about 100 μM Stauprimide, alternatively about 100 nm to about 10 μM, alternatively about 200 nM to about 1 μM, alternatively about 200 nm to about 500 nM and suitable amounts and ranges in between.

In another embodiment, the method of maturing immature hepatocytes comprises culturing the immature hepatocytes with at least one c-myc inhibitor, preferably Stauprimide wherein the immature hepatocytes after culturing have at least two-fold reduction in the expression of an alpha-fetoprotein (AFP) and express one or more mature hepatocyte genes at a minimum level of at least 70% the level of that gene found in fresh primary hepatocytes.

Method of Producing a Substantially Pure Population of Hepatic Cells

Another embodiment of the disclosure provides a method for generation of an essentially pure population of hepatocytes from pluripotent cells using a chemically defined differentiation medium. A chemically defined differentiation medium allows for the ability to use the hepatocytes in screens without the fear of presence of interfering compounds sometimes found in media. Up until now, differentiation of hepatocytes from pluripotent stem cells has led to generation of non-hepatic cells within the culture, and thus to obtain an essentially pure population, the hepatocytes would have to be either selected or sorted from the cellular population.

In one aspect, the method of culturing a substantially pure population of hepatocytes from pluripotent cells comprises culturing the pluripotent cells in a defined medium comprising at least one inhibitor of transforming growth factor (TGF) 3 and at least one inhibitor of NOTCH, wherein the culturing generates a substantially pure population of hepatocytes expressing asialoglycoprotein receptor 1 (ASGR1). In some embodiments, the substantially pure population of hepatocytes expresses ASGR1 and albumin.

As used herein, the term "substantially pure" refers to a population of hepatic cells that is at least about 80%, more suitably at least about 90% (e.g., at least about 80%, 85%, 90%, 95%, 98%, 99% or more) pure, with respect to expressing the ASGR1 gene and/or albumin. In other words, the term "substantially pure" refers to a population of hepatocytes that contains fewer than about 20%, about 10%, about 5%, or about 2% of non-hepatic cells (e.g. cells that do not express ASGR1 and/or albumin) when directing differentiation to obtain the hepatocyte cells from a pluripotent cell population. In some cases, a substantially pure isolated population of hepatocytes generated according to a method provided herein is at least about 95% (e.g., at least about 95%, 96%, 97%, 98%, 99%, 100%) pure with respect to expression of at least the ASGR1 gene and/or albumin. In some embodiments, the substantially pure hepatocyte population is at least about 95% (e.g., at least about 95%, 96%, 97%, 98%, 99%, 100%), pure with respect to expression of both ASGR1 and albumin. In some instances, the method provides a population that is at least 98% pure with respect to expression of ASGR1 gene, in some instances at least 98% pure with respect to expression of ASGR1 gene and albumin. In some instances, the method provides a population that is at least 99% pure with respect to expression of ASGR1 gene, in some instances at least 99% pure with respect to expression of ASGR1 gene and albumin.

In some aspects, the culturing step comprises culturing the pluripotent stem cells to definitive endoderm cells and further culturing the definitive endoderm cells in defined medium comprising at least one inhibitor of (TGF)-β and at least one inhibitor of NOTCH.

Methods of differentiating pluripotent stem cells to definitive endoderm are known in the art, for example, culturing the pluripotent stem cells in defined medium comprising Activin A. A suitable method of differentiating pluripotent stem cells to definitive endoderm includes, but is not limited to, methods described in D'Amour et al, Nat. Biotechnol., 23 (2005) pp. 1534-1541, incorporated by reference in its entirety.

Suitable concentrations of Activin A for use in the methods and kits include, but are not limited to, for example, at least 10 ng/ml, alternatively about 50 ng/ml Activin A, preferably at least about 100 ng/ml Activin A. In some embodiments, the Activin A concentration is about 10 ng/ml to about 1000 ng/ml, alternatively about 10 ng/ml to about 500 ng/ml, alternatively about 10 ng/ml to about 150 ng/ml, alternatively about 50 ng/ml to about 1000 ng/ml, alternatively about 50 ng/ml to about 500 ng/ml, alternatively about 50 ng/ml to about 200 ng/ml Activin A, alternatively about 50 ng/ml to about 150 ng/ml, including any amounts and ranges in between the forgoing, for example, about 50 ng/ml, about 75 ng/ml, about 100 ng/ml, about 150 ng/ml.

Once the cells have been differentiated into definitive endoderm, the cells may be further differentiated into hepatocytes. The method of further differentiating the definitive endoderm into hepatocytes comprises culturing the cells in defined medium comprising at least one inhibitor of (TGF)-β and at least one inhibitor of NOTCH and factors known in the art to differentiate endoderm cells into hepatic cells. There are a number of published protocols for differentiating definitive endoderm cells into hepatic endoderm, most of which culture the definitive endoderm cells in a culture medium that includes both fibroblast growth factor-4 (FGF4) and bone morphogenetic protein-2 (BMP2). A non-limiting example of a published protocol to differentiate definitive endoderm to fetal hepatic endoderm is that disclosed by J. Cai et al. (Hepatology (2007) 45: 1229-1239), which is incorporated by reference in its entirety.

In one suitable embodiment, the definitive endoderm cells are cultured in defined medium and a fibroblast growth factor (FGF) and a bone morphogenic protein (BMP), and then the cells are cultured in defined medium and a hepatocyte growth factor (HGF) and Oncostatin M (OSM). In one suitable embodiments, the definitive endoderm cells are cultured with FGF4 or FGF10 from day 8 to day 12 of the culture and further cultured in a defined medium comprising hepatocyte growth factor (HGF) and Oncostatin M (OSM) from day 13 through 17 of the culture.

Suitable concentrations of FGF for use in the methods and kits include, but are not limited to, for example, from about 1 ng/ml to about 500 ng/ml FGF, alternatively about 1 ng/ml to about 100 ng/ml FGF, alternatively about 10 ng/ml to about 500 ng/ml FGF, alternatively about 10 ng/ml to about 100 ng/ml FGF, including, but not limited to, e.g., 10 ng/ml, 20 ng/ml, 25 ng/ml, 30 ng/ml, 40 ng/nl, 50 ng/ml, 75 ng/ml, 100 ng/m, 150 ng/ml, 200 ng/ml, and amounts and ranges in between.

Suitable concentrations of BMP for use in the methods and kits include, but are not limited to, for example, from about 5 ng/nl to about 500 ng/ml BMP, alternatively about 1 ng/ml to about 100 ng/ml BMP, alternatively about 10 ng/ml to about 500 ng/ml FGF, alternatively about 10 ng/ml to about 100 ng/ml FGF, including, but not limited to, e.g., 10 ng/ml, 20 ng/ml, 25 ng/ml, 30 ng/ml, 40 ng/ml, 50 ng/nl, 75 ng/nl, 100 ng/mi, 150 ng/ml, 200 ng/ml, and amounts and ranges in between. In one embodiment, the BMP is BMP2. In one preferred embodiment, the amount of BMP2 is about 10 ng/ml to about 50 ng/ml, preferably about 20 ng/ml.

Suitable concentrations of HGF for use in the present methods and kits include, but are not limited to, for example, from about 2 ng/ml to about 200 ng/ml HGF, alternatively about 2 ng/ml to about 100 ng/ml HGF, alternatively about 10 ng/ml to about 200 ng/ml FGF, alternatively about 10 ng/ml to about 100 ng/ml FGF, including, but not limited to, e.g., 10 ng/ml, 20 ng/ml, 25 ng/ml, 30 ng/ml, 40 ng/ml, 50 ng/ml, 75 ng/ml, 100 ng/ml, 150 ng/ml, 200 ng/ml, and amounts and ranges in between. In a preferred embodiment, the concentration of HGF is about 10 ng/ml to about 50 ng/ml, for example, 20 ng/ml.

Suitable concentrations of Oncostatin for use in the methods and kits include, but are not limited to, for example, from about 5 ng/ml to about 100 ng/ml, preferably about 5 ng/ml to about 50 ng/ml, alternatively about 5 ng/ml to about 20 ng/ml, and any suitable amount or range in between. In one embodiment, the concentration if Oncostatin is about 5 ng/ml to about 25 ng/ml, suitably 10 ng/ml.

The method of producing a substantially pure population of hepatocytes may further comprise culturing the cells with dexamethasone. Dexamethasone can be added anytime after formation of definitive endoderm cells. Suitably, dexamethasone may be added at day 18 through at least day 22 of culture. In another embodiment, the dexamethasone is added anytime after day 8, e.g. after endoderm formation.

Suitable concentration of dexamethasone used in the methods and kits include, but are not limited to, about 0.05M to about 0.5M, preferably about 0.05 to about 0.2M, alternatively about 0.1M to about 0.2M. In a preferred embodiment, the concentration of dexamethasone used is about 0.1M.

Methods of making pure populations of cells from differentiating pluripotent cells usually rely on methods of isolating the selected population from other cells that may be found in the differentiated culture. Method of isolating the cells include, for example, but are not limited to cell sorting for specific surface markers or genetic selection. The methods of the present disclosure are advantageous as the method does not comprise a step of isolating, genetically selecting or sorting the cultured hepatocyte cells from non-hepatocytes. The cells that are differentiated from the pluripotent cells are substantially pure and homogenous, expressing ASGR1 and albumin.

The human pluripotent cells used in these methods can be human embryonic stem cells or human induced pluripotent stem cells. Human embryonic stem cells are derived from the inner cell mass of the human blastocyst. Induced pluripotent stem cells are a type of pluripotent stem cell artificially derived from a non-pluripotent cell, typically an adult somatic cell, by inducing a "forced" expression of certain genes. Either type of human pluripotent cell can be used in the method.

Suitable TGF-β inhibitors are known in the art and include, but are not limited to, for example, SB431542, A 83-01, RepSox, SD 208, SB 505124, Ly 364947, R 268712, D 4476, SB 525334, GW 788388, among others. In a preferred embodiment, the TGF-β inhibitor is SB431542.

Suitable concentrations of TGF-β inhibitors used in the present methods and kits include, but are not limited to, about 10 nm to about 10 mM, alternatively about 10 nm to about 2 mM, alternatively from about 10 nm to about 1 mM, alternatively from about 10 nm to about 500 μM, alternatively from about 100 nm to about 2 mM, alternatively from about 100 nm to about 200 μM, alternatively about 1 μM to about 200 μM of the TGF-β inhibitor, alternatively about 1 μM to about 100 μM, alternatively from about 5 μM to about 20 μM, alternatively about 5 μM to about 15 μM, alternatively about 5 μM to about 10 μM. In one embodiment, the TGF-β inhibitor is used in an amount of about 10 μM.

Suitable NOTCH inhibitors are known in the art, and include, but are not limited to, for example, DAPT, FLI-06 (Cyclohexyl 2,7,7-trimethyl-4-(4-nitrophenyl)-5-oxo-1,4,6,8-tetrahydroquinoline-3-carboxylate), LY3039478, among others.

Suitable concentrations of NOTCH inhibitors used in the present methods and kits include, but are not limited to, 10 nm to about 10 mM, alternatively about 10 nm to about 2 mM, alternatively from about 10 nm to about 1 mM, alternatively from about 10 nm to about 500 μM, alternatively from about 100 nm to about 2 mM, alternatively from about 100 nm to about 1000 μM, alternatively about 100 nm to about 500 μM, alternatively about 1 μM to about 20 μM of the NOTCH inhibitor. In one embodiment, the NOTCH inhibitor concentration is from about 5 μM to about 20 μM, alternatively about 5 μM to about 15 μM, alternatively about 5 μM to about 10 μM. In another embodiment, the NOTCH inhibitor is used in an amount of about 10 μM.

The terms "defined culture medium," "defined medium," and the like, as used herein, indicate that the identity and quantity of each medium ingredient is known. As used herein, the terms "chemically-defined culture conditions," "fully defined, growth factor free culture conditions," and "fully-defined conditions" indicate that the identity and quantity of each medium ingredient is known and the identity and quantity of supportive surface is known. As used herein, the term "albumin-free" indicates that the culture medium used contains no added albumin in any form, including without limitation Bovine Serum Albumin (BSA) or any form of recombinant albumin.

Standardizing culture conditions by using a chemically defined culture medium minimizes the potential for lot-to-lot or batch-to-batch variations in materials to which the cells are exposed during cell culture. Accordingly, the effects of various differentiation factors are more predictable when added to cells and tissues cultured under chemically defined conditions. As used herein, the term "serum-free" refers to cell culture materials that do not contain serum or serum replacement, or that contain essentially no serum or serum replacement. For example, an essentially serum-free medium can contain less than about 1%, 0.9%, 0.8%, 0.7%, 0.6%, 0.5%, 0.4%, 0.3%, 0.2%, or 0.1% serum. "Serum free" also refers to culture components free of serum obtained from animal (e.g., fetal bovine) blood or animal-derived materials, which is important to reduce or eliminate the potential for cross-species viral or prion transmission. For avoidance of doubt, serum-containing medium is not chemically defined.

Preferably, each culturing step for producing essentially pure hepatocyte population is performed using defined medium under chemically defined, xeno-free, and albumin-free conditions. For purposes of this disclosure, "xeno-free" means having no xenogeneic products of non-human animal origin, such as cells, tissues and/or body fluids, or any tissue or blood components, such as serum, which contain variable and undefined factors. Xeno-free medium and culture substrates are made up of known or "defined" components, which reduces the risk of viral contamination, prion transmission, and the batch-to-batch variability that is present using an undefined medium. Accordingly, for human cells, a xeno-free culture medium is defined as a culture medium essentially free of animal components, wherein the animal is not a human.

Suitable defined medium includes, but is not limited to, E6 medium.

In some embodiments, the essentially pure population of hepatocytes is further cultured in defined medium comprising at least one MAPK inhibitor. Not to be bound by any theory, further culturing of the essentially pure population with MAPK inhibitor is thought to maintain the differentiation of the hepatocyte population.

The disclosure further provides an essentially pure population of hepatocytes expressing ASGR1 and albumin produced by the methods herein.

In still a further embodiment, the disclosure provides a composition comprising the substantially pure population of hepatocytes expressing ASGR1 and albumin and at least one MAPK inhibitor.

The disclosure also encompasses methods of using the hepatocytes produced by the disclosed methods in toxicity testing and in treating patients having a liver disorder or liver cancer.

The present disclosure encompasses a method for testing the potential toxicity of a compound. In one embodiment, such a method includes the steps of (a) exposing one or more hepatocytes produced by the method described above to the compound, and (b) monitoring the one or more hepatocytes for signs of toxicity. In another embodiment, such a method includes the steps of (a) exposing one or more hepatocytes produced by the method described above to the compound, wherein the compound is metabolized by the hepatocytes; (b) contacting the resulting metabolite(s) of the compound with one or more non-hepatocyte cells; and (c) monitoring the non-hepatocyte cells for any metabolite-induced changes. Non-limiting examples of non-hepatocyte cells that could be used in the method include neurons or cardiomyocytes.

In some embodiments, the present disclosure provides methods of determining metabolites of a test compound. Such a method includes the steps of (a) exposing one or more hepatocytes produced by the method described above to the compound; and (b) determining what metabolites are produced by the hepatic processing of the compound. In addition to testing the toxicity of a test compound on the hepatocytes themselves, the hepatocyte medium containing the metabolite(s) of the test compound may be taken and put on cultures of non-hepatocytes.

For example, liver cell metabolites may be subsequently tested on cardiomyocytes (for cardiotoxicity testing) or on cultures of neurons (for neurotoxicity testing). Testing on the non-hepatocyte cells may occur either in a co-culture, or with a conditioned medium. This is a useful method for testing certain drugs that are not toxic in themselves, but which may be converted to a toxic form by the liver. For example, certain liver metabolites of non-toxic compounds are known to block the hERG channel in the heart, causing arrhythmias. However, the method is not limited by this example, and can be broadly applied to a variety of non-hepatocyte cell types.

Such methods include the step of monitoring the hepatocytes or non-hepatocytes for signs of potential toxicity. The cells need not be directly observed, and this step encompasses a variety of methods for assaying potential cellular damage or dysfunction caused by exposure to a test compound. Monitoring for signs of toxicity may include, without limitation, testing for the levels of certain biomarkers or gene expression products, testing cellular function, and directly observing the structure of the cells. As a non-limiting example, elevated levels of certain biochemical markers (e.g., alanine transferase, alkaline phosphatase, and bilirubin) can indicate toxicity in hepatocytes. Furthermore, cellular apoptosis, changes in cellular morphology, or the transformation of cells into a neoplastic form may result from induced toxicity. The method is not limited to any particular monitoring technique, and encompasses any such techniques used in the art.

Regarding methods of treating liver disorders, the hepatocytes produced by the disclosed methods may be used either short term or long term in patients wherein an orthotopic liver transplant would be desirable. Transplantation of functional hepatocytes may save many lives, as there is a severe shortage of livers for transplantation, resulting in large number of deaths to patients on liver transplant waiting lists. For example, functional hepatocytes could be used for treatment of liver metabolic disorders such as alpha-1-antitrypsin deficiency and Wilson's disease, where in severe cases, orthotopic liver transplant is currently the only recourse. Furthermore, in cases of acute liver damage (such as from drug overdose), hepatocyte transplantation may also save lives. Finally, hepatocyte transplantation may help people on transplant waiting lists live long enough to receive an organ (i.e., bridge transplantation).

Finally, MAP kinase inhibitors may be useful in managing liver cancer, which has one of the poorest prognoses. With progression, hepatocellular carcinoma becomes dedifferentiated with concomitant increase in malignancy. Maintenance of differentiated state of the tumor and arrest of growth may prolong survival.

Kits

Aspects of the present disclosure that are described with respect to methods can be utilized in the context of the compositions or kits discussed in this disclosure. Similarly, aspects of the present disclosure that are described with respect to the compositions can be utilized in the context of the methods and kits, and aspects of the present disclosure that are described with respect to kits can be utilized in the context of the methods and compositions.

This disclosure provides kits. The kits can be suitable for use in the methods described herein.

Suitable kits include a kit for maturing human hepatocytes comprising: (i) medium suitable or sufficient for culturing hepatocytes and (ii) at least one MAPK inhibitor. The kit further may include instructions on how to culture hepatocytes. In some embodiments, the kits further include a culture dish. In some embodiments, the kit may further include suitable hepatocytes for culturing. Suitable hepatocytes include primary human hepatocytes or immature human hepatocytes.

Another embodiment provides a kit for growing hepatitis virus in culture, the kit including (i) medium sufficient for culturing hepatocytes, (ii) at least one MAPK inhibitor and instructions for growing hepatitis virus. The kit may further comprise a hepatitis virus. In some embodiments, the kit further comprises suitable hepatocytes for culturing. Additionally, the kit may include culture dishes.

In another embodiment, the disclosure provides kit for culturing an essentially pure population of mature hepatocytes from human pluripotent cells, the kit comprising (i) defined medium sufficient for differentiation of the pluripotent cells into hepatocytes; and (ii) at least one inhibitor of TGF-0 and (iii) at least one inhibitor of NOTCH. In some embodiments, the kit further comprises additional components to be added to the defined medium sufficient to allow for the differentiation of the pluripotent cells to hepatocytes, for example, Activin A, FGF4, BMP (e.g. BMP2), HGF, Oncostatin, dexamethasone, and combinations thereof. The additional components can be added to the defined medium at different time points according to the instructions. Suitably, the kit can be used to perform the method described above.

In some embodiments, the kits described about may further include a culture dish. In some embodiments, the kit may further include suitable human hepatocytes for culturing. Suitable human hepatocytes may be fresh or frozen cells.

The following non-limiting examples are included for purposes of illustration only, and are not intended to limit the scope of the range of techniques and protocols in which the compositions and methods of the present invention may find utility, as will be appreciated by one of skill in the art and can be readily implemented.

The present invention has been described in terms of one or more preferred embodiments, and it should be appreciated that many equivalents, alternatives, variations, and modifications, aside from those expressly stated, are possible and within the scope of the invention.

EXAMPLES

Example 1: Maintenance and Maturation of Hepatocytes

Cultured primary human hepatocytes (PHHs) are an indispensable tool for drug development and toxicity testing, but lack of availability and short viability in vitro has hindered their use. This is primarily due to the fact that they dedifferentiate in culture and lose their mature phenotype (i.e. expression of mature hepatic [drug metabolism and other adult liver function-associated] genes). The inventors identified let-7c, a developmental timing-associated microRNA, to be associated with hepatocyte differentiation whose transduction in PHHs arrested the loss of mature hepatic genes and inhibited their dedifferentiation in culture. The inventors predicted let-7c target kinase pathways (MAPK, PI3/Akt) were downregulated in let-7c transduced PHHs.

This Example demonstrates that inhibitors of MAPK pathway are able to maintain mature hepatic gene expression in cultured mature hepatocytes and also to induce the expression of mature hepatic gene expression in immature hepatic cells. Specifically, this Example demonstrates that U0126, a small molecule inhibitor of the MAPK pathway, but not LY294002, an inhibitor of PI3/Akt pathway, is able to maintain mature hepatic gene expression in cultured primary mouse hepatocytes. U0126 also maintained mature hepatic gene expression in cultured PHHs and greatly upregulated/induced their expression in HepG2, a fetal hepatoma cell line. U0126 increased drug metabolism in HepG2 and induced the expression of Hepatitis B and C virus receptors making them potentially susceptible to infection.

This Example also demonstrates that PD0325901, another MAPK inhibitor, inhibited loss of mature hepatic gene expression of PHHs in culture confirming MAPK's specific role in maintaining hepatic maturity. This example also shows that MAPK inhibition by U0126 successfully maintains PHH maturity in vitro and drives fetal human hepatocytes towards maturity. These results greatly aid drug development by extending the viability of PHHs in culture as well as making an easily cultured and abundant hepatic cell line useful for drug testing.

PHHs are known to lose their mature phenotype shortly after isolation or removal from their in vivo environment (1). Attempts to maintain long-term maturity of PHHs in culture, or to mature fetal hepatic cells, have shown limited success. Culture systems designed to mimic the hepatocyte microenvironment (sandwich and aggregate cultures) and co-culture methods with other non-parenchymal liver cells have not been able to significantly enhance the viability of cultured PHHs or mature fetal hepatocytes (ibid). While oncogenically transformed hepatic cell lines such as HepG2 have the advantage of being abundant, expandable, and easy to culture, their use in in vitro liver modeling is limited as they are fetal in nature, refractory to infection by hepatotropic viruses, and a poor metabolizer of xenobiotics due to a lack of, or low levels of, many phase I and II enzymes and drug transporters (2).

In this study, cellular maturation was looked at from a developmental point of view. Maturation is brought about by the temporal expression of developmental timing-associated genes in vivo and possibly orchestrated by gene(s) that are more highly expressed during later developmental stages. The inventors hypothesized that the expression of these late genes would increase during liver development and would decrease during dedifferentiation, similarly as to when they are in culture or during liver cancer progression, and that the forced expression of these genes in fetal or immature hepatocytes would drive them towards a mature phenotype. MicroRNAs control expression of a large number of genes and pathways and are good candidates as modulators of maturity (3). After thorough examination of mircoRNA let-7c was identified as strongly associated with hepatic maturation and as a regulator of mature hepatic genes. One category of genes that are targets of let-7c are MAP kinases.

This Example demonstrates the surprising result that inhibition of MAP kinases by various small molecules reduces loss of maturity of PHHs in culture as well as drives maturation of the fetal hepatoma cell line HepG2. This simple method of maturing an abundant fetal cell line will diminish obstacles of PHH availability for use in in vitro liver models and facilitate drug development. Moreover, inhibition of dedifferentiation by small molecules will open avenues for liver cancer management.

Results

MicroRNA let-7c is Associated with Hepatic Maturation. MicroRNAs are proficient gene regulators. A single microRNA can influence multiple genes in a pathway and thus modulate that pathway. In this study, the potential of microRNAs in regulating pathways involved in hepatic differentiation/maturation was explored. Comprehensive sequencing of all small RNAs in mature PHHs and primary mouse hepatocytes revealed that multiple let-7 family members were among the top 20 expressed microRNAs in both species, with let-7c having the highest expression in PHHs and let-7f having the second highest expression in mouse (Table 1). The liver-specific microRNA mir-122 is the second most highly expressed microRNA in humans and the most highly expressed microRNA in mice. Redundant high expression of multiple let-7s, a broadly conserved microRNA family across diverse species, suggests an important biological role for this microRNA. To explore the potential relationship with hepatocyte maturation, let-7c was chosen for further study because all of the highly expressed let-7 members belonged to the 5' end of the pri-miRNA stem loop (let-7-5p), had a similar overall sequence, and had the exact same seed sequence making them functionally equivalent (4).

TABLE 1

Highly expressed microRNAs in primary human and mouse hepatocytes

| Human hepatocytes | | Mouse hepatocytes | |
|---|---|---|---|
| MicroRNA | Normalized Read | MicroRNA | Normalized Read |
| hsa-let-7c | 63269 | mmu-miR-122-5p | 3272173 |
| hsa-miR-122 | 60961 | mmu-let-7f-5p | 76605 |
| hsa-miR-378c | 36754 | mmu-miR-192-5p | 66781 |
| hsa-miR-143 | 32569 | mmu-miR-148a-3p | 47428 |
| hsa-miR-148a | 29138 | mmu-let-7g-5p | 39539 |
| hsa-miR-21 | 23047 | mmu-miR-22-3p | 29872 |
| hsa-miR-192 | 17119 | mmu-let-7a-5p | 25111 |
| hsa-let-7f | 16756 | mmu-miR-26a-5p | 22047 |
| hsa-miR-30d | 8251 | mmu-miR-21a-5p | 21081 |
| hsa-miR-146b-5p | 5788 | mmu-miR-99a-5p | 19754 |
| hsa-miR-30e | 5123 | mmu-let-7c-5p | 13551 |
| hsa-miR-126 | 5067 | mmu-miR-10a-5p | 10921 |
| hsa-miR-27b | 4943 | mmu-miR-126a-3p | 10849 |
| hsa-miR-30a | 4747 | mmu-miR-27b-3p | 7673 |
| hsa-let-7i | 4423 | mmu-miR-101a-3p | 5378 |
| hsa-miR-194 | 4335 | mmu-let-7b-5p | 4219 |
| hsa-miR-107 | 3382 | mmu-let-7i-5p | 4134 |
| hsa-miR-26a | 3073 | mmu-let-7d-5p | 3815 |
| hsa-miR-10a | 2870 | mmu-miR-143-3p | 3498 |
| hsa-miR-24 | 2439 | mmu-miR-378a-3p | 3107 |

MicroRNA reads were normalized to total microRNA counts.

This study involved ascertaining the level of expression of let-7 in dedifferentiating cultured primary hepatocytes to determine its association with hepatic maturation. RNA was collected from freshly isolated hepatocytes derived from mouse livers after perfusion and culturing for 24, 48 and 72 hours. RNA from livers resected just after sacrifice was also used. FIG. 1*a*(*i*) shows gradual decrease of let-7c in cultured hepatocytes over time as cells dedifferentiate. Interestingly, it also indicates loss of the microRNA after the cells were singularized by perfusion that was partially recovered in fully confluent cultures. A similar loss of let-7c was also found over time in dedifferentiating cultured PHHs isolated from multiple donors (FIG. 1*a*(*ii*)). Notably, let-7c expression in PHHs was three orders of magnitude higher than in the fetal HepG2 cells. These results indicate a correlation between hepatic differentiation/maturation with microRNA let-7c.

Next, human liver cancer, or hepatocellular carcinoma (HCC), was studied in which tumors are initially well differentiated before gradually dedifferentiating and losing mature hepatic functionality. Tissue samples containing HCC, which were derived from 19 individuals, were obtained from the archives of the University of Wisconsin-Madison's Department of Pathology. The degree of cellular differentiation in these samples was classified by morphological criteria as normal, very well differentiated, moderately well differentiated, moderately differentiated, moderate-poorly differentiated, or poorly differentiated in 31 tissue regions. These 31 regions were harvested by laser microdissection and let-7c expression was measured by qPCR. Let-7c expression was significantly greater in regions classified as normal and lessened with declining grades of differentiation; thus, showing a correlation between let-7c expression and hepatocyte maturation status (Figure Tb). Lastly, let-7c expression in relation to liver development in mice was explored. Because of the possible presence of the hematopoietic compartment in embryonic livers, only post-natal livers were used. Postnatal mouse livers were isolated at two time points (day 6.5 and day 12.5) and the expression of let-7c was measured. At postnatal day 6.5, when the liver is somewhat mature and contains fetal hepatocytes for metabolizing macromolecules from the mother's milk, the level of expression of let-7c was lower than the level of expression at postnatal day 12.5 when the liver is fully mature; again demonstrating the positive correlation of let-7c expression and liver development (FIG. 1*c*).

Figures 2A, 2B, 2C:
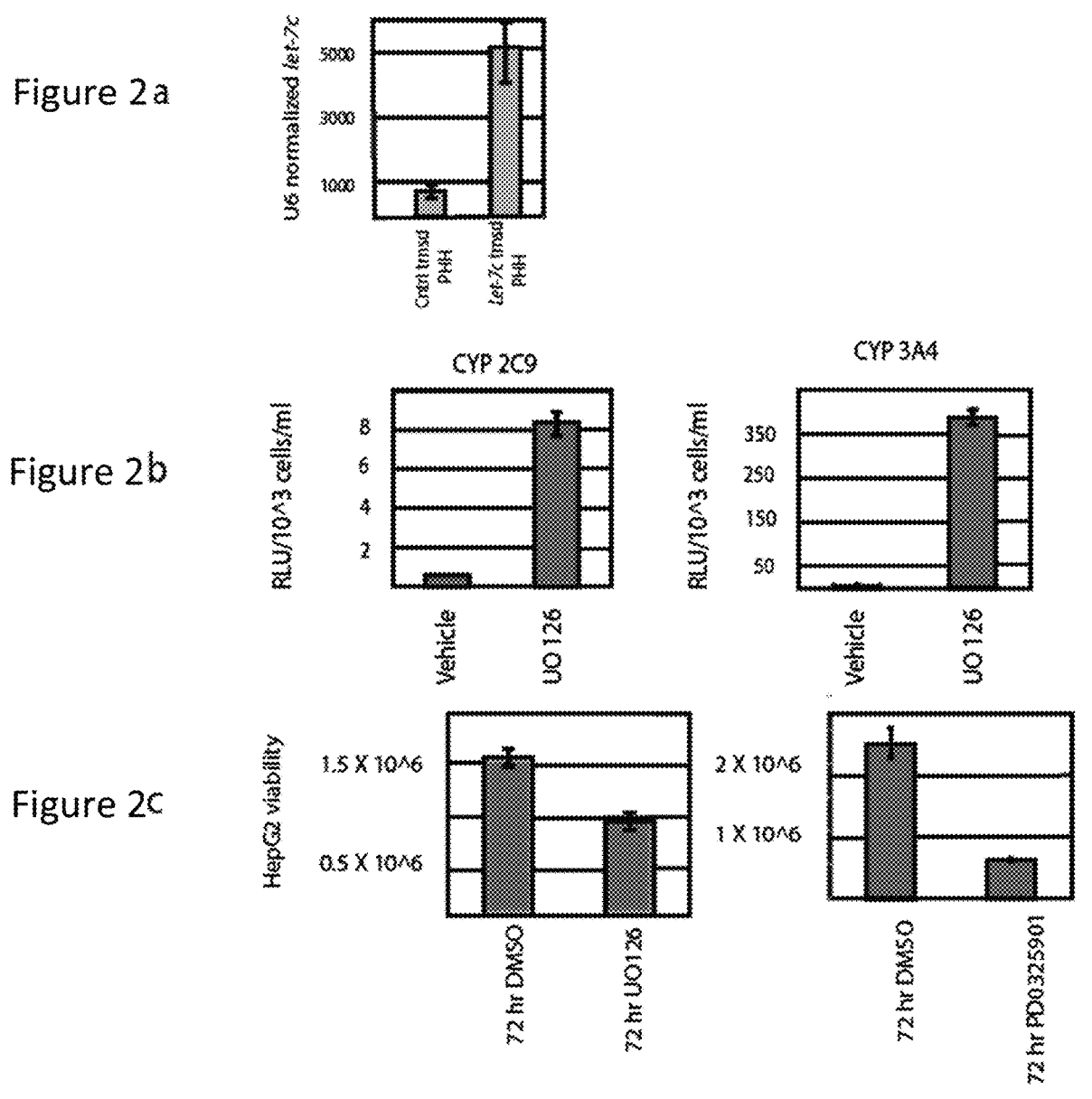

Let-7c Upregulates Mature Hepatic Genes. To determine if let-7c is causally associated with hepatic differentiation/maturation, the inventors inquired whether it can maintain mature hepatic gene expression in cultured dedifferentiating PHHs. let-7c and a control scrambled microRNA tagged with fluorescent markers were transduced into PHHs with lentiviruses and cultured them for 72 hours. Approximately 25% of cells displayed marker expression and the let-7c transduced cell population showed ~5-fold higher levels of the microRNA compared to negative control transductions (FIG. 2*a*). After performing whole genome RNA-Seq, it was found that mature hepatic genes (major phase I and II metabolic enzymes, transporters, and other hepatic functional genes) lost their expression by 72 hours in culture (Table 2). Let-7c partially or fully rescued the expression of the majority of these genes and in some cases upregulated them to even higher levels than normal. Importantly, let-7c downregulated the expression of AFP, a fetal gene whose expression increased during dedifferentiation. This validates that let-7c is not only associated with, but also contributes to, maintenance of differentiated phenotype of hepatocytes.

TABLE 2

Gene expression of control and let-7c transduced primary human hepatocytes

| Gene | Uncultured PHHs | Control Transduced PHHs at 72 hours | Let-7c transduced PHHs at 72 hours |
|---|---|---|---|
| CYP1A2 | 73.27 | 3.83 | 10.53 |
| CYP1B1 | 2.74 | 2.93 | 21.02 |
| CYP2C9 | 479.92 | 22.56 | 73.91 |
| CYP2D6 | 118.35 | 4.85 | 17.07 |
| CYP2E1 | 2790.51 | 14.73 | 32.08 |
| CYP3A4 | 324.67 | 7.15 | 2.98 |
| UGT1A1 | 218.49 | 35.23 | 49.39 |
| UGT1A6 | 447.52 | 333.03 | 235.17 |
| UGT1A9 | 26.27 | 57.01 | 81.43 |
| SLCO1B1 | 38.53 | 18.77 | 56.42 |
| SLCO1B3 | 18.31 | 12.66 | 0.85 |
| ALB | 21426.68 | 1324.31 | 4736.40 |
| AFP | 0.64 | 9.81 | 4.49 |
| APOA1 | 7521.92 | 578.43 | 2662.19 |
| ADH4 | 337.74 | 7.64 | 26.30 |
| TAT | 307.78 | 6.99 | 14.71 |
| TTR | 2526.14 | 272.27 | 399.68 |

PHH, primary human hepatocyte.
Gene expression values are given in transcripts per million.

Kinase Signaling Pathways Are Targets of let-7c. Transduction is an inefficient and arduous process. To circumvent this, the inventors wanted to identify let-7c targeted genes/pathways that could be manipulated by small molecule mimics for hepatocyte differentiation. A microRNA can downregulate its direct targets as well as downstream genes and so a comprehensive look at all genes/pathways modulated by let-7c was necessary. It was found that let-7c downregulated 2007 genes in cultured PHHs by 2-fold or more (expressed at 2 or more TPM) compared to control transduction. Differentially expressed genes were identified by calculating fold expression changes between let-7c and control transduced PHHs, both at 72 hours to control for gene downregulation caused by dedifferentiation. MicroRNAs target multiple genes in a pathway to elicit its effect. Signal transduction pathways modulate cellular response to their microenvironment, and since hepatocyte maturation is associated with their environmental status (i.e., in vivo or ex vivo), pathways analysis was used to identify signaling pathways that may be targeted by let-7c to modulate hepatocyte maturation. Pathways analysis with KEGG (5, 6) of the 2007 let-7c modulated genes was performed and it was found that two signal transduction pathways (MAPK and PI3/Akt) among the top ten pathways overrepresented among those genes (the others were metabolic pathways, pathways in cancer, regulation of actin cytoskeleton, focal adhesion, proteoglycans in cancer, HTLV1 infection, microRNAs in cancer, and endocytosis). Let-7c targeted multiple genes in both kinase pathways (29 and 26 genes in the PI3/Akt and MAPK pathways respectively).

MAP Kinase Inhibition Reduces Dedifferentiation of Primary Hepatocytes and Matures HepG2. The next step was to determine if the PI3/Akt and MAPK pathways are involved in maintenance of hepatocyte maturation. We investigated whether small molecule inhibition of these pathways would mimic let-7's action and reduce the loss of mature function of hepatocytes in culture after removal from their microenvironment. Primary mouse hepatocytes were treated either individually, or in combination, with U0126 and LY294003 (inhibitors of MAPK and PI3/Akt pathways respectively) at 10 μM concentrations. Then, expression of the top ten important metabolic enzymes (CYPs, UGTs and transporters) by RNA-Seq with uncultured fresh hepatocytes and control vehicle hepatocytes treated for 72 hours was compared. (Table 3). We found that U0126, a MAPK inhibitor, not only maintained the expression of metabolic enzymes at 72 hours in culture, but upregulated some of them at higher levels than fresh hepatocytes. LY294003 also inhibited loss of maturation to some extent but did not elicit as great a response as U0126 at the tested concentration. Thus, MAPK inhibition appears to maintain metabolic maturity of hepatocytes.

Next, primary human hepatocytes and a fetal hepatoma cell line, HepG2, were treated with U0126 to investigate its effect on human hepatic cells. Both types of cells were treated with a vehicle or small molecule for 72 hours and genes were quantified using RNA-Seq. U0126 not only maintained metabolic and other hepatic gene expression in the primary human hepatocytes, but it significantly upregulated or induced high expression of these genes in HepG2 cells where expression was previously absent. It upregulated major phase I and II enzymes as well as transporters making them metabolically functional. Importantly, U0126 downregulated the fetal gene AFP significantly (over 3 orders of magnitude) in both cell types (Table 4) compared with the untreated control.

TABLE 3

Gene expression changes in mouse hepatocytes treated with kinase inhibitors

| | Treatment | | | | |
|---|---|---|---|---|---|
| Gene | Uncul-tured | Vehicle control, 72 hours | U0126, 72 hours | LY294002, 72 hours | UOP126 + LY294002, 72 hours |
| CYP1A2 | 326.79 | 27.49 | 1271.98 | 80.54 | 1241.42 |
| CYP2C9 | 873.55 | 455.52 | 2676.68 | 1332.65 | 3390.35 |
| CYP2E1 | 5785.13 | 69.08 | 217.96 | 57.37 | 164.70 |
| CYP3A11 | 799.36 | 265.44 | 632.32 | 1409.71 | 859.42 |
| CYP3A25 | 147.68 | 29.00 | 112.18 | 61.42 | 102.44 |
| UGT1A10 | 7.34 | 0.00 | 2.44 | 0.86 | 0.38 |
| UGT1A6A | 73.47 | 63.05 | 232.80 | 48.21 | 232.65 |
| UGT1A9 | 88.32 | 66.93 | 184.63 | 15.27 | 100.130 |
| UGT2B5 | 1892.24 | 571.29 | 995.27 | 196.44 | 681.90 |
| ABCC2 | 128.06 | 106.88 | 415.86 | 232.34 | 570.03 |

Gene expression values are given in transcripts per million.

TABLE 4

Metabolic and other hepatic gene expression in U0126 treated HepG2 and primary human hepatocytes

| | HepG2 | | Primary human hepatocytes | | |
|---|---|---|---|---|---|
| Gene | Vehicle control treated, 72 hours | U0126 treated, 72 hours | Uncultured | Vehicle control treated, 72 hours | U0126 treated, 72 hours |
| CYP1A2 | 0.16 | 0.68 | 374.43 | 1.69 | 68.21 |
| CYP1B1 | 0.00 | 3.07 | 1.78 | 0.10 | 30.96 |
| CYP2C9 | 0.00 | 33.45 | 1131.77 | 0.27 | 77.04 |
| CYP2D6 | 3.70 | 4.05 | 107.2.0 | 1.00 | 1.81 |
| CYP2E1 | 0.00 | 14.61 | 5101.44 | 0.00 | 17.69 |
| CYP3A4 | 0.00 | 13.37 | 1175.71 | 1.00 | 43.64 |
| UGT1A1 | 6.16 | 16.61 | 118.17 | 2.23 | 47.57 |
| UGT1A6 | 10.53 | 835.05 | 724.26 | 1.92 | 671.53 |
| UGT1A9 | 0.00 | 99.71 | 32.89 | 0.00 | 81.41 |
| SLCO1B1 | 0.00 | 120.17 | 124.35 | 0.00 | 153.15 |
| SLCO1B3 | 0.00 | 18.83 | 73.82 | 0.00 | 14.65 |
| ALB | 8735.62 | 2083.6 | 58510.31 | 12886.74 | 1360.25 |
| AFP | 6727.43 | 4.74 | 1.76 | 2256 | 5.79 |
| SLC10A1 | 0.00 | 10.57 | 180.63 | 0.00 | 0.00 |
| CD81 | 0.93 | 634.68 | 495.15 | 0.67 | 417.56 |

Gene expression values are given in transcripts per million.

We next looked at two important drug metabolizing enzymes and their ability to metabolize drugs. CYP3A4 and CYP2C9 derived from HepG2 cells were treated with U0126 or a vehicle control. U0126 was found to upregulate metabolite formation over 30- and 10-fold for CYP3A4 and 2C9 respectively confirming that U0126 indeed increases functionality of HepG2 cells (FIG. 2*b*). Thus, MAPK inhibition is able to significantly extend the useful life of primary cells in culture allowing detection of minor metabolites. Importantly, MAPK inhibition made HepG2s functional which would make them usable for drug development and therefore lessen reliance on the use of primary cells.

Finally, to ensure that upregulation of functional genes by U0126 was not a side-effect of the drug, we inhibited MAPK kinases by a second small molecule, PD0325901, in primary human hepatocytes. We found that it did minimize the drastic loss of expression of hepatic metabolic genes (Table 5) as evidenced by RNA-Seq of the hepatocytes, which were cultured with the small molecule or a vehicle for 72 hours. We then compared these results to those obtained using uncultured hepatocytes, confirming that the arrest of loss of maturation occurs through the specific inhibition of the MAPK signaling pathway. PD0325901, like U0126, also downregulated the fetal gene AFP. Thus, it was concluded that MAPK inhibition reduces the loss of metabolic maturity of cultured primary hepatocytes and induces maturity in fetal hepatocytes.

TABLE 5

Metabolic and other hepatic gene expression in PD0325901 treated primary human hepatocytes

| Gene | Uncultured PHHs | Vehicle control treated PHHs, 72 hours | PD0325901 treated PHHs, 72 hours |
|---|---|---|---|
| CYP1A2 | 374.43 | 1.69 | 1.87 |
| CYP1B1 | 1.78 | 0.10 | 3.56 |
| CYP2C9 | 1131.77 | 0.27 | 73.61 |
| CYP2D6 | 107.20 | 1.00 | 1.24 |
| CYP2E1 | 5101.44 | 0.00 | 4.94 |
| CYP3A4 | 1175.71 | 1.00 | 22.44 |
| UGT1A1 | 118.17 | 2.23 | 69.02 |
| UGT1A6 | 724.26 | 1.92 | 1337.30 |
| UGT1A9 | 32.89 | 0.00 | 87.51 |
| SLCO1B1 | 124.35 | 0.00 | 151.48 |
| SLCO1B3 | 73.82 | 0.00 | 7.24 |
| ALB | 58510.31 | 12886.74 | 1293.62 |
| AFP | 1.76 | 2256.00 | 7.07 |
| CD81 | 495.15 | 0.67 | 388.31 |

PHH, primary human hepatocyte.
Gene expression values are given in transcripts per million.

U0126 Upregulates Viral Receptors in HepG2. HepG2s are refractory to infection by hepatotropic viruses, and the only cell line which allows productive infection, HepaRG, requires maturation by treatment with DMSO for an extended period of time. We looked at SLC10A1 and CD81, hepatitis B virus (HBV) and hepatitis C virus (HCV) receptors, respectively, in U0126 treated HepG2 cells, and found them to be significantly induced where they were previously absent (>1 TPM) (Table 4). Thus, U0126 treated HepG2 cells would potentially open up a simple system for study of HBV and HCV as well as allow for development of antivirals in readily available and easily culturable cells. Also, U0126 treatment resulted in significant inhibition of cell growth in HepG2s (FIG. 2*c*), a process which may be useful for treatment and management of liver cancer. The HCV receptor was upregulated in U0126 and PD0325901 treated primary hepatocytes and the HBV receptor was upregulated in PD0325901 treated cells (Table 4 and 5).

Discussion

PHHs are indispensable for the development of in vitro liver models for the study of liver disease and viruses and in toxicity testing and drug development. However, despite the extensive research over the past half-century, a simple system for maintaining the functional maturity of PHHs in culture has yet to be established. Additionally, aims to develop a process for the maturation of fetal hepatocytes have also been unsuccessful. Since the loss of mature hepatocyte function is thought to be associated with the isolation from their specific microenvironment in the liver as cell to cell contact maintains liver functional enzymatic activity (7), attempts have been made to manipulate culture conditions, such as 3D culture and heterotypic co-culture, in order to mimic in vivo conditions. While these systems have yielded various levels of improvement in maintaining hepatic function ex vivo, they have not generated successful fetal hepatocyte maturation. A recent study (8) shows the capability of oncostatin M (OSM) to maintain the mature phenotype of PHHs in culture, but the process entails extensive genetic manipulation of the PHHs requiring HPV E6/E7 transduction and arduous colony screening in order to identify clones that can be matured. Furthermore, this method was not shown to mature fetal hepatocytes. Conditions that enable both the maintenance of PHH maturity and the maturation of fetal hepatocytes are necessary to overcome limited availability of PHHs and make fetal hepatic cell lines and hepatocytes derived from pluripotent stem cells functional. Overcoming the limitations of the scarce availability of PHHs by maturing fetal cells would not only significantly aid the pharmaceutical pursuit of drug and antiviral development, but would also greatly benefit the process of organ fabrication and the development of methods for rapid toxicity testing such as body-on-a-chip.

Here, we report the discovery that let-7c, a developmental timing-associated microRNA, maintains the differentiated hepatic phenotype in vitro, and additionally, that mimicking let-7c targeting of MAPK signaling pathway by small molecules not only reduces the loss of maturity of PHHs in culture, but also induces fetal cell maturation. This simple method to maintain and generate functional hepatocytes would be tremendously useful to many aspects of the industry in regards to addressing the problem of unavailability of primary cells for drug development and toxicity testing.

Let-7 was one of the first microRNAs to be discovered and hence has been the most studied. It is a well-known evolutionarily conserved regulator of developmental timing and executor of temporal events during development in many organisms, from nematodes to zebrafish (9, 10, 11, 12). In particular, let-7c has been hypothesized to confer maturation as it inhibits reprogramming of somatic cells to pluripotent cells (9). This hypothesis is strengthened by the fact that let-7c is absent from pluripotent cells and is repressed by LIN28 (13), an essential factor for the reprogramming of somatic cells into induced pluripotent stem cells (14). Recently, let-7 has also been shown to mature cardiomyocytes (3).

We found multiple members of the let-7 family to be abundantly expressed in mature tissues pointing to an important biological role through redundancy. Furthermore, to reinforce its role in regulating maturation, let-7c targeted multiple genes in the MAPK signaling pathway, which has previously been postulated to be an important target pathway of let-7c (15). Hepatocyte dedifferentiation involves epithelial-mesenchymal transition (EMT) (8, 16). MAPK inhibition by U0126 blocks EMT (17, 18, 19). Thus, it is likely that the observed maturation of hepatocytes in our work brought about by U0126 happened in whole or part through prevention of EMT. This is further strengthened by the observation in breast cancer cells of suppression of EMT by let-7 through MAPK inhibition (20Q2Q).

Another important facet of our work reported here is induction of HBV and HCV virus receptors by MAPK inhibition. This would potentially open up a simple system for study of hepatotropic viruses. HBV and HCV studies as well as the development of drugs to treat the diseases are hampered by the lack of a simple culture system. Pluripotent stem cell derived hepatocytes have been shown to allow infection but require differentiation which costs time. HepaRG cells also require a long maturation period in culture to be receptive to infection. Our findings present an easier system for study of these viruses as well as aid development of anti-virals for treatment of HBV/HCV-associated diseases.

Materials and Methods

Human Liver Cancer Sample Processing. Human liver cancer (hepatocellular carcinoma) tissue samples from 19 deceased patients were obtained from the archives of the University of Wisconsin-Madison Department of Pathology and Laboratory Medicine after obtaining necessary Institutional Review Board waivers. A total of 31 tissue regions having varying grades of cellular differentiation (including non-cancerous normal tissue) marked by the pathologist were laser microdissected. Tissues were harvested in buffer PKD with proteinase K (miRNeasy FFPE Kit, Qiagen) and heated for 15 minutes at 55° C. followed by another 15 minutes at 80° C. Finally, total RNA was isolated with Trizol.

Mouse Liver Sample Processing. Hepatocytes from 6 black mice livers were isolated by perfusion following standard protocol and cultured on Matrigel coated plates in hepatocyte growth medium (Promocell). Whole developing livers from 6 black mice were used for RNA isolation with Trizol for let-7c measurements.

Primary Human Hepatocytes. Cryopreserved induction qualified human hepatocytes were purchased from Life Technologies and cultured on Matrigel™ coated plates in hepatocyte growth medium (PromoCell). For small RNA-Seq profiling, hepatocytes from Hu8082 were used; for de-differentiation time course and let-7c transduction, hepatocytes from Hu4260, Hu8135, Hu4279 and Hu8137 were used. For both experiments, cells from all 4 donors were mixed in equal numbers after assessment of viability. For small molecule treatments, batch Hu4260 was used.

Lentiviral Transduction. Scrambled control microRNA (Applied Biological Materials, GFP reporter) transducing lentiviruses were packaged as per manufacturer's kit instructions. For let-7c transduction, prepackaged lentiviral particles were purchased from Biosettia. Transduction was performed by incubating the cells with lentiviruses at 4° C. for 1 hour followed by incubation at 37° C. for further 23 hours with 1 mM HEPES and 4 μg/ml polybrene.

Gene Expression Analysis. Total RNA (including microRNA) from all cells, which were not mentioned otherwise, were isolated using RNAeasy Plus Kit (Invitrogen) following manufacturers protocol. RNA-Seq was performed by LM-Seq (Illumina). MicroRNAs were sequenced using Illumina's small RNA sequencing kit. Expression of let-7 and U6 snoRNA were measured by quantitative PCR using ABI's kit. Let-7c expression levels were normalized by U6 snoRNA expression (RQ or relative quantity values, error bars representing standard error, RQ min and RQ max).

Drug metabolism testing. HepG2 cells cultured in DMEM/F12 with 10% FBS were incubated with DMSO or U0126 for 72 hours. CYP2C9 and 3A4 metabolism were measured using CYP450 Glo assay (Promega). In short, substrates were added to the media and incubated for 72 hours and the amount of metabolites generated were measured by adding the detection reagent and quantifying the luminescence in a Tecan® plate reader. Background was measured by incubating the substrates for 72 hours in the same media without cells. Cell counting for proliferation assay was carried out by dye exclusion in an automated cell counter (ThermoFisher).

References for Example 1

1. In vitro models for liver toxicity testing. (2013). Soldatow V Y, Lecluyse E L, Griffith L G, Rusyn. *Toxicol Res* (*Camb*). 2(1): 23-39.

2. Characterization of primary human hepatocytes, HepG2 cells, and HepaRG cells at the mRNA level and CYP activity in response to inducers and their predictivity for the detection of human hepatotoxins. (12). Gerets H H, Tilmant K, Germ B, Chanteux H, Depelchin B O, Dhalluin S, Atienzar F A. *Cell Biol Toxicol.* 28(2):69-87.

3. Let-7 family of microRNA is required for maturation and adult-like metabolism in stem cell-derived cardiomyocytes. (2015). Kuppusamy K T, Jones D C, Sperber H, Madan A, Fischer K A, Rodriguez M L, Pabon L, Zhu W Z, Tulloch N L, Yang X, Sniadecki N J, Laflamme M A, Ruzzo W L, Murry C E, Ruohola-Baker H. *Proc Natl Acad Sci USA.* 112(21): E2785-94.

4. Predicting effective microRNA target sites in mammalian mRNAs. (2015). Agarwal V, Bell G W, Nam J W, Bartel D P. Elife. 4. doi: 10.7554/eLife.05005.

5. KEGG: kyoto encyclopedia of genes and genomes. (2000). Kanehisa M, Goto S. *Nucleic Acids Res.* 28(1): 27-30.

6. KEGG as a reference resource for gene and protein annotation. (2016). Kanehisa M, Sato Y, Kawashima M, Furumichi M, Tanabe M. *Nucleic Acids Res.* 44(D1): D457-62.

7. Regulation of cell morphology and cytochrome P450 expression in human hepatocytes by extracellular matrix and cell-cell interactions. (2001). Hamilton G A, Jolley S L, Gilbert D, Coon D J, Barros S, LeCluyse E L. *Cell Tissue Res.* 306(1): 85-99.

8. Long-term culture and expansion of primary human hepatocytes. (2015). Levy G, Bomze D, Heinz S, Ramachandran S D, Noerenberg A, Cohen M, Shibolet O, Sklan E, Braspenning J, Nahmias Y. *Nat Biotechnol.* 33(12): 1264-1271.

9. Developmental timing: let-7 function conserved through evolution. (2008). Tennessen J M, Thummel C S. *Curr Biol.* 18(16): R707-8.

10. MicroRNAs and developmental timing. (2011). Ambros V. *Curr Opin Genet Dev.* 21(4): 511-7

11. The 21-nucleotide let-7 RNA regulates developmental timing in *Caenorhabditis elegans*. (2000). Reinhart B J, Slack F J, Basson M, Pasquinelli A E, Bettinger J C, Rougvie A E, Horvitz H R, Ruvkun G. *Nature.* 403 (6772): 901-6.

12. Conservation of the sequence and temporal expression of let-7 heterochronic regulatory RNA. (2000). Pasquinelli A E, Reinhart B J, Slack F, Martindale M Q, Kuroda M I, Maller B, Hayward D C, Ball E E, Degnan B, Müller P, Spring J, Srinivasan A, Fishman M, Finnerty J, Corbo J, Levine M, Leahy P, Davidson E, Ruvkun G. *Nature.* 408(6808): 86-9.

13. Lin28 mediates the terminal uridylation of let-7 precursor MicroRNA. (2008). Heo I, Joo C, Cho J, Ha M, Han J, Kim V N. *Mol Cell.* 32(2): 276-84.

14. Induced pluripotent stem cell lines derived from human somatic cells. (2007). Yu J, Vodyanik M A, Smuga-Otto K, Antosiewicz-Bourget J, Frane J L, Tian S, Nie J, Jonsdottir G A, Ruotti V, Stewart R, Slukvin I I, Thomson J A. *Science.* 318(5858): 1917-20.

15. A dictionary on microRNAs and their putative target pathways. (2010). Backes C, Meese E, Lenhof H P, Keller A. *Nucleic Acids Res.* 38(13): 4476-86.

16. Mature hepatocytes exhibit unexpected plasticity by direct dedifferentiation into liver progenitor cells in culture. (2012). Chen Y, Wong P P, Sjeklocha L, Steer C J, Sahin M B. *Hepatology.* 55(2): 563-74.

17. ERK1/2 blockade prevents epithelial-mesenchymal transition in lung cancer cells and promotes their sensitivity to EGFR inhibition. (2014). Buonato J M, Lazzara M J. *Cancer Res.* 74(1): 309-19.

18. Snail promotes epithelial mesenchymal transition in breast cancer cells in part via activation of nuclear ERK2. (2104). Smith B N, Burton L J, Henderson V, Randle D D, Morton D J, Smith B A, Taliaferro-Smith L, Nagappan P, Yates C, Zayzafoon M, Chung L W, Odero-Marah V A. *PLoS One.* 9(8): e104987.

19. Oncostatin M-induced effects on EMT in human proximal tubular cells: differential role of ERK signaling. (2007). Pollack V, Sarkozi R, Banki Z, Feifel E, Wehn S, Gstraunthaler G, Stoiber H, Mayer G, Montesano R, Strutz F, Schramek H. *Am J Physiol Renal Physiol.* 293(5): F1714-26.

20. Stat3-coordinated Lin-28-let-7-HMGA2 and miR-200-ZEB1 circuits initiate and maintain oncostatin M-driven epithelial-mesenchymal transition. (2013). Guo L, Chen C, Shi M, Wang F, Chen X, Diao D, Hu M, Yu M, Qian L, Guo N. *Oncogene.* 32(45): 5272-82.

Example 2: Defined Differentiation of Pure Hepatocytes from Human Embryonic Stem Cells This Example provides a method for generation of a pure population of authentic hepatocytes using a chemically defined differentiation medium from pluripotent cells. We have identified a chemically defined differentiation medium which allows for the ability to use the differentiated hepatocytes in screens without the fear of presence of interfering compounds sometimes found in media.

Here we demonstrate the derivation of hepatocytes from ES cells in a defined medium and identify TGFB and NOTCH pathways to block differentiation to the hepatic lineage, inhibition of which generated a uniform population of hepatocytes. This is a big step forward in our effort to generate functional hepatocytes from pluripotent stem cells.

Up until now, differentiation of hepatocytes from pluripotent stem cells has led to generation of non-hepatic cells. Using a marker cell line that expressed GFP and tdTomato under albumin and alpha feto-protein promoters respectively (ALB-GFP/tdTomato-AFP), we identified TGF-beta and NOTCH pathways which specify non-hepatic lineages during hepatocyte differentiation from human embryonic stem cells (ES cells). We discovered that the inhibition of the TGF-beta and NOTCH pathways generated a uniform and pure population of hepatocytes in a chemically defined medium. These cells not only morphologically resembled cultured primary human hepatocytes, but flow cytometric analysis with ASGR1, a hepatocyte specific cell surface protein, showed over 95% of these cells to be true hepatocytes. Further, we differentiated the ALB-GFP/tdTomato-AFP marker cell line which upon treatment with U0126 (a MAP kinase inhibitor that matures fetal hepatocytes) showed 100% positivity for both markers, thus confirming generation of pure and true hepatocytes. Thus, by inhibiting TGF-beta and NOTCH pathways, we generated a pure population of hepatocytes from ES cells in defined medium.

Results

TGFB and NOTCH pathways higher in non-hepatic cells. Signaling pathways orchestrate lineage specification during development and to study pathways involved in hepatic fate specification in vitro, we generated a dual marker cell line that expresses green fluorescent protein driven by the mature hepatic gene Albumin (ALB) locus along with tdTomato fluorescent protein driven by the fetal hepatic gene Alpha-fetoprotein (AFP) locus (ALB-GFP/tdTomato-AFP) by transfecting the construct into H9 cells (FIG. 3). We differentiated this line to hepatocytes using a previously published protocol (Reference 1) and flow-sorted AFP, ALB, dual ALB/AFP positive as well as cells negative for both markers. All four fractions were profiled by RNA-Seq with the exception of ALB positive cells that were too few to yield sufficient RNA. We looked for differential expression of major developmentally important signaling pathways (TGFB, NOTCH, WNT etc.) between the hepatic (AFP, AFP/Alb positive cells) and non-hepatic fraction (cells negative for both markers) and found TGFB and NOTCH ligands/receptors to be higher in non-hepatic cells indicating they may negatively regulate hepatic fate.

Figure 5:
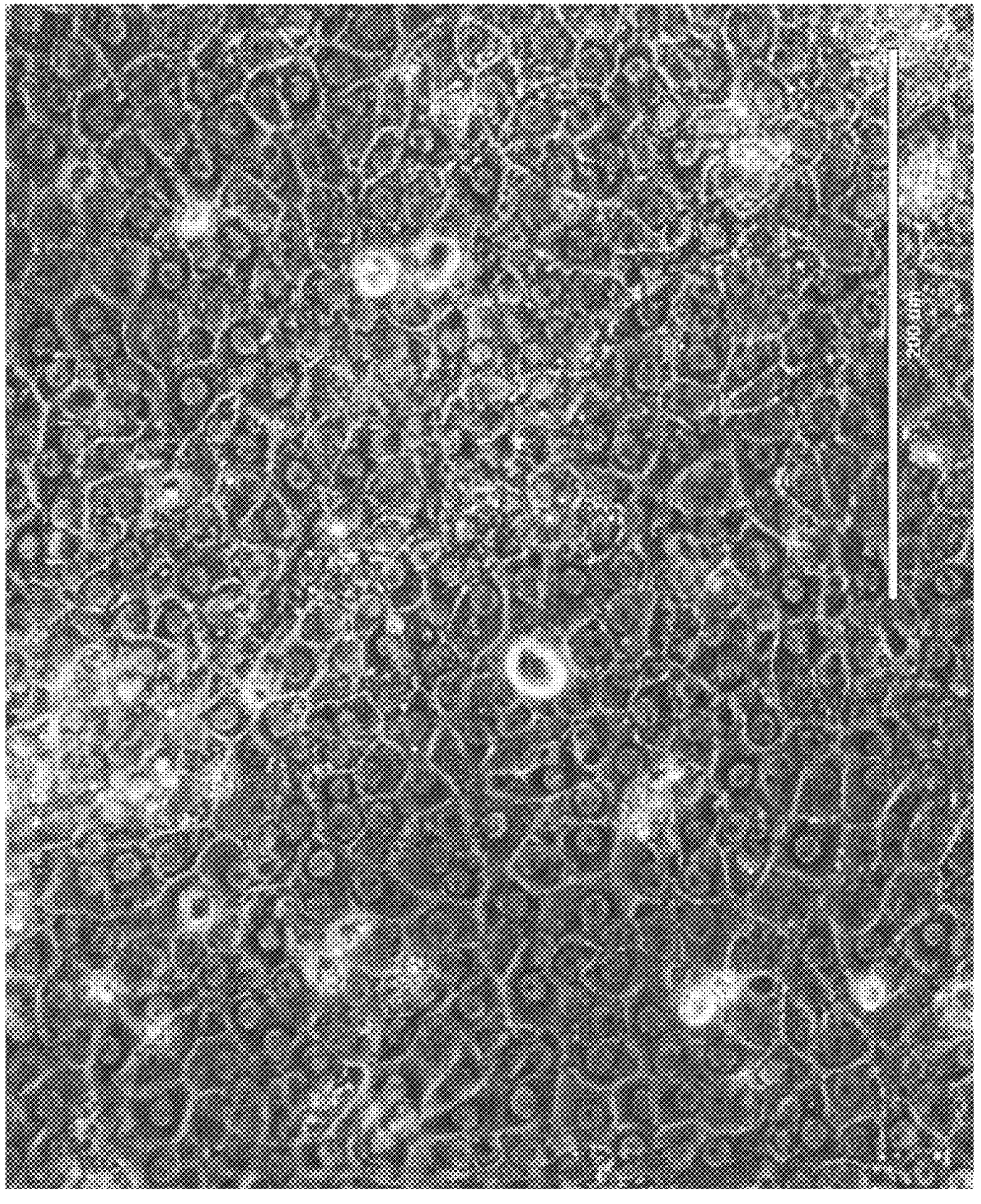
FIG. 5. Morphology of hepatocytes differentiated from ES cells in defined media with TGFB and NOTCH inhibition.
Figure 6:
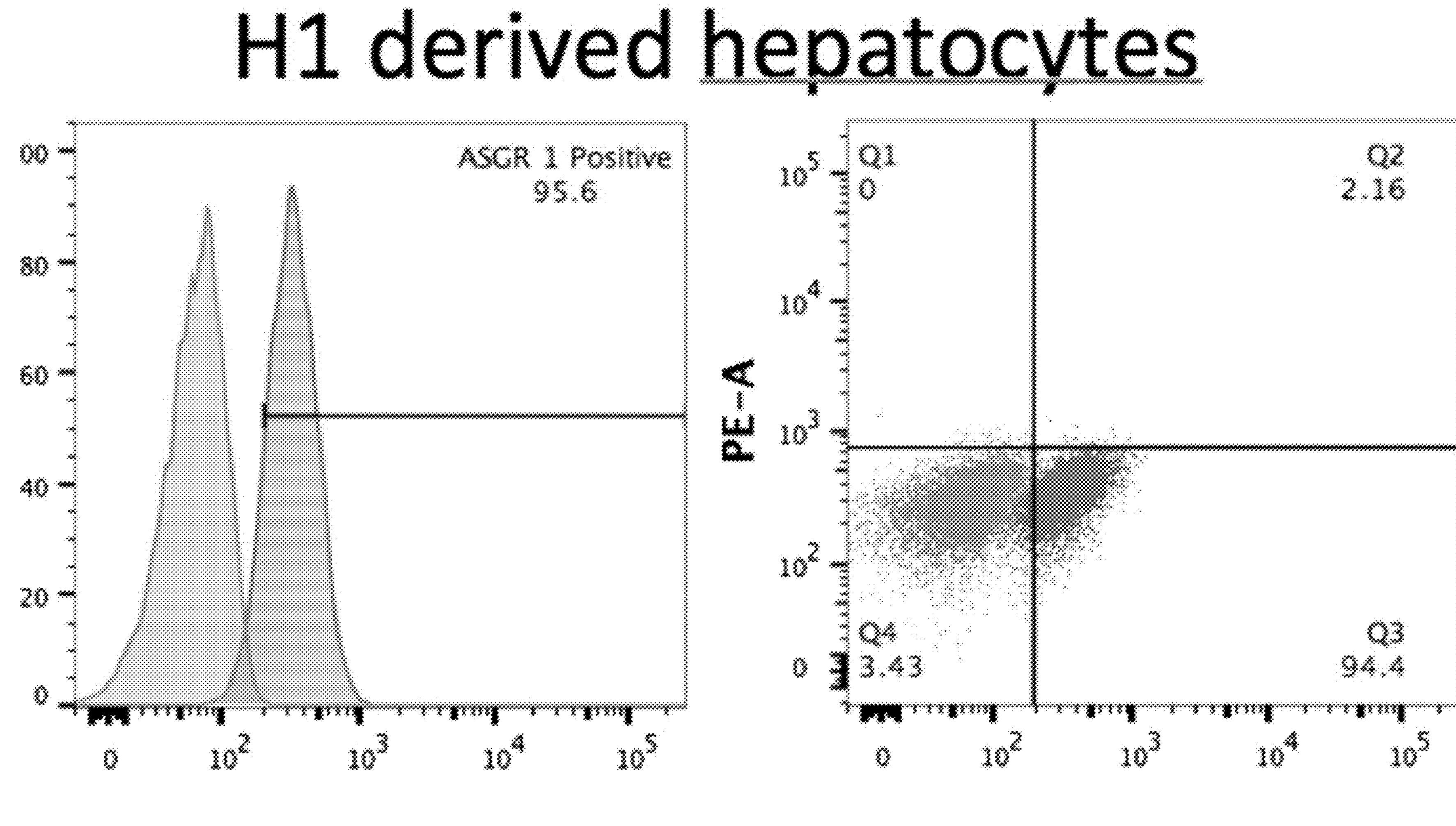
FIG. 6. Flow analysis of percentage of hepatocytes generated from H1 ES cells by a hepatocyte specific cell surface marker, ASGR1.
Figure 7:
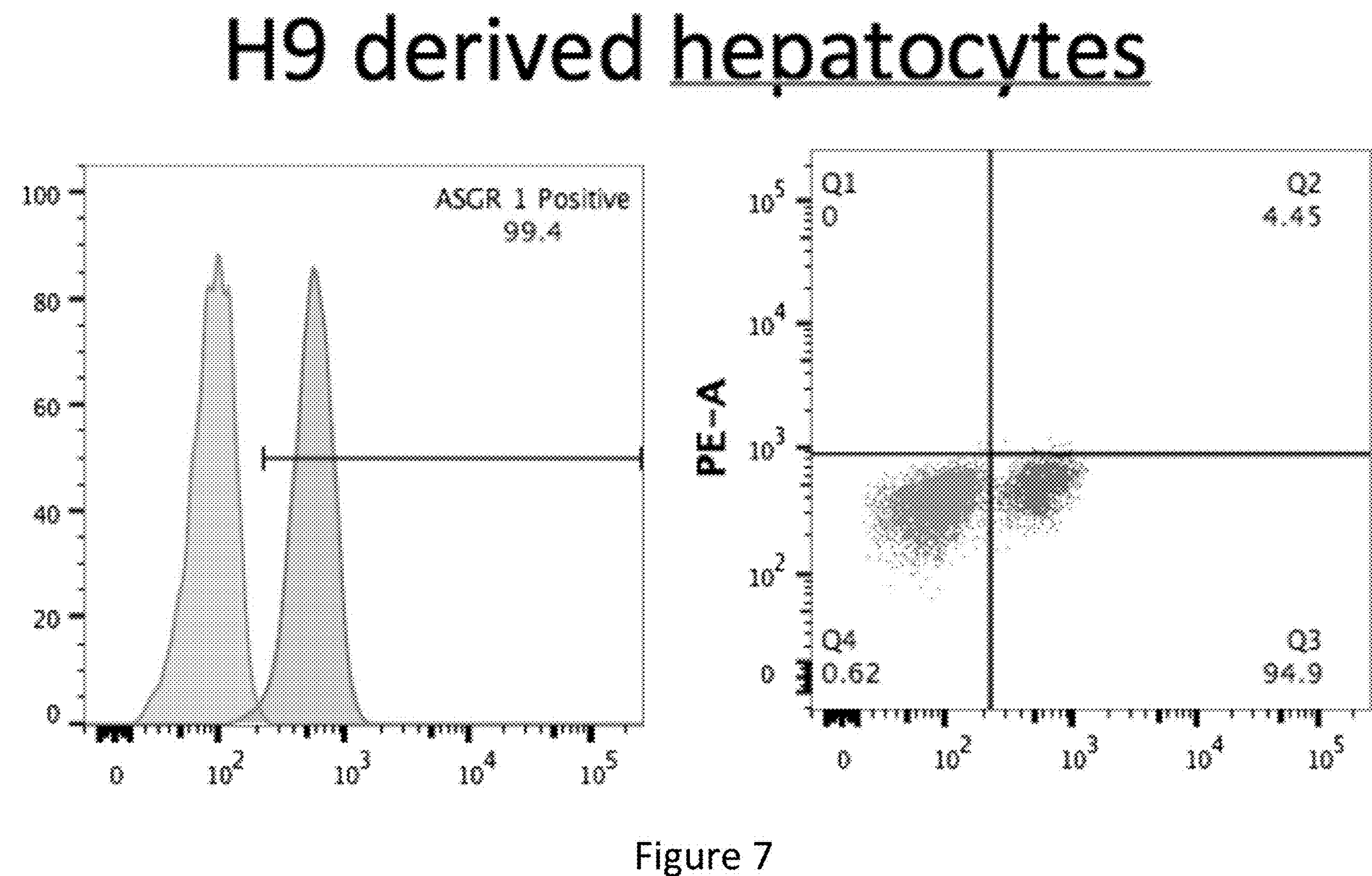
FIG. 7. Flow analysis of percentage of hepatocytes generated from H9 ES cells sorted by a hepatocyte specific cell surface marker, ASGR1.

TGFB, NOTCH pathway inhibition generates pure hepatocytes from ES cells. To explore whether TGFB and NOTCH pathway inhibition by small molecules would increase the efficiency of hepatocyte generation from ES cells, we needed a defined medium for differentiation that would not have compounds that may be antagonists of small molecule inhibitors of these pathways. We chose E6 medium as our basal differentiation medium, which is E8 medium used for ES cell culture (Reference 2) sans TGFB and FGF. For hepatic differentiation, cells were seeded after disassociation by Accutase™ to single cells on Matrigel™ coated plates. A previously published protocol was followed broadly with some modifications (Reference 1 and FIG. 4). Albumin was removed from the medium and Activin A treatment was performed for a longer duration and TGFB and NOTCH were inhibited by addition of SB431542 and DAPT at 10 μm final concentrations respectively after generation of definitive endoderm (detailed in Materials and Methods). Hepatocytes generated thus were dramatically different than the ones generated by previous protocol. The differentiated cells uniformly displayed hepatocyte morphology that very closely resembled cultured primary hepatocytes in morphology (FIG. 5). Not only were the cells morphologically uniform, they also uniformly expressed the hepatic cell surface marker ASGR1. H1 and H9-derived hepatocytes were 95 and 99% positive for ASGR1 by flow cytometric analysis (FIG. 6 and FIG. 7).

Figure 8A:
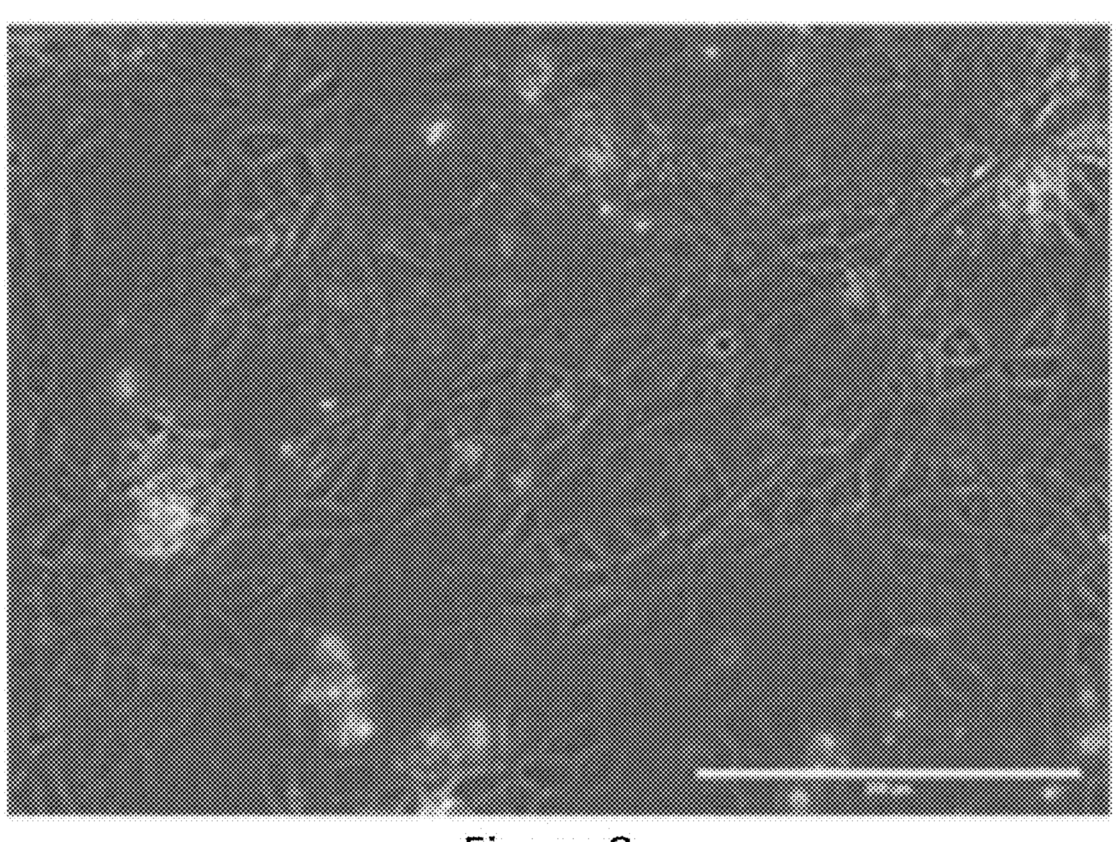
FIG. 8*a*. Bright field image of albumin and alpha-fetoprotein (AFP) expression (as evidenced by GFP and tdTomato expression) in ALB-GFP/tdTomato-AFP marker cell line differentiated with TGFB and NOTCH inhibition.
Figure 8B:
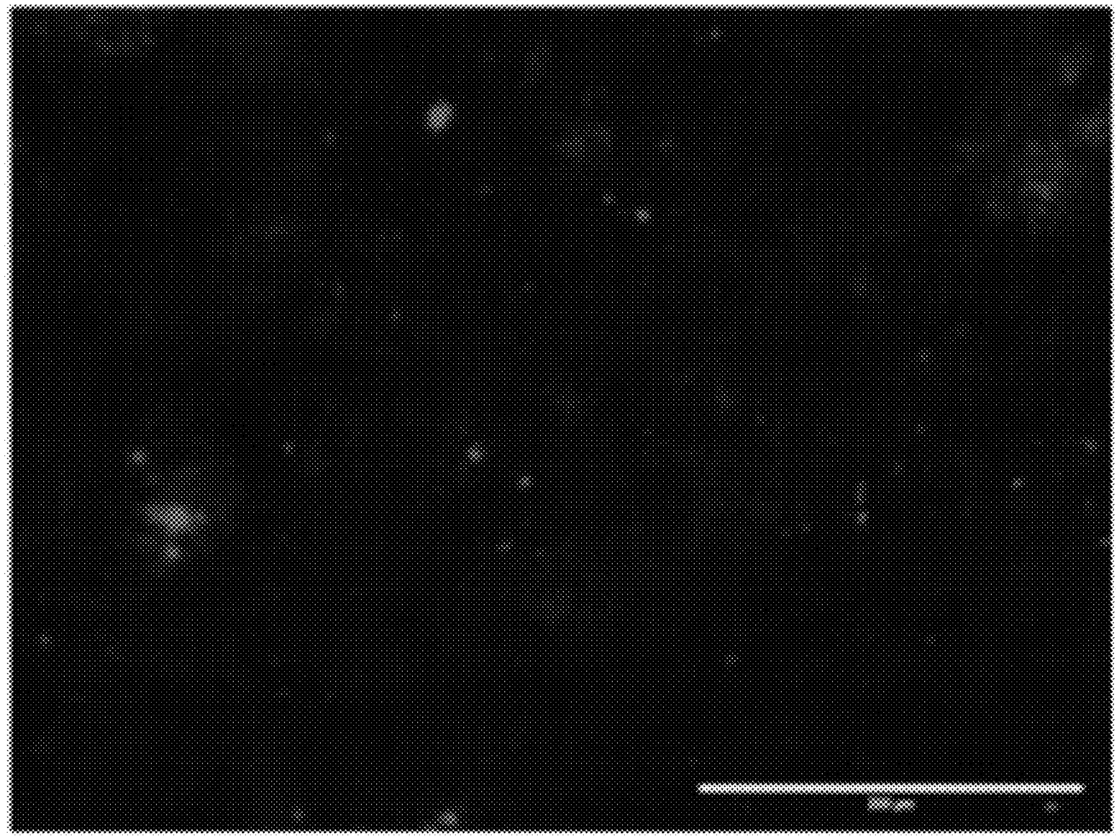
FIG. 8*b*. Image of AFP staining (as evidenced by tdTomato expression) in ALB-GFP/tdTomato-AFP marker cell line differentiated with TGFB and NOTCH inhibition.
Figure 8C:
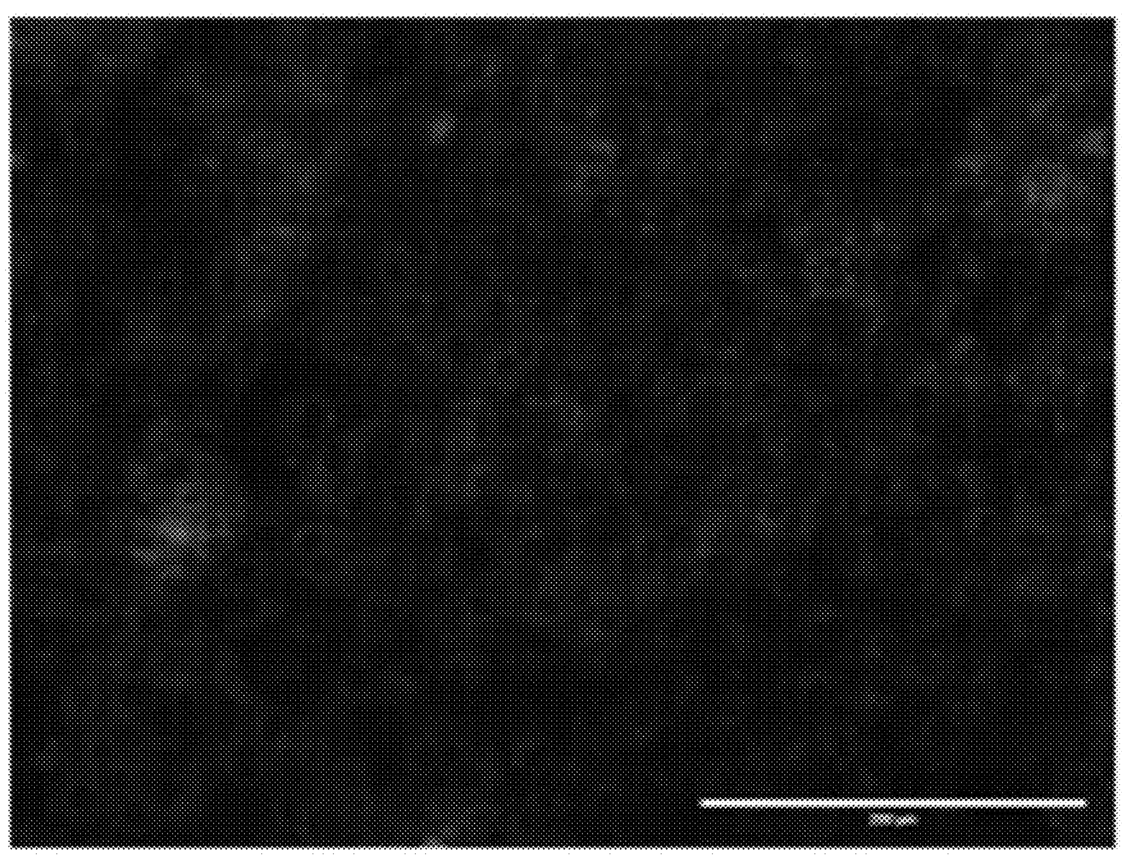
FIG. 8*c*. Image of albumin staining (as evidenced by GFP expression) in Albumin and AFP expression (as evidenced by GFP and tdTomato expression) in ALB-GFP/tdTomato-AFP marker cell line differentiated with TGFB and NOTCH inhibition.

ALB-GFP/tdTomato-AFP marker cell line differentiated with TGFB and NOTCH inhibition expresses ALB and AFP uniformly. We next differentiated the ALB-GFP/tdTomato-AFP marker cell line to hepatocytes with TGFB and NOTCH inhibition in defined E6 medium. At the end of the differentiation period, we added U0126, a MAP Kinase inhibitor for 72 hours that upregulates hepatic genes such as Albumin. U0126 treatment resulted in 100% of the cells expressing both ALB and AFP (FIG. 8) confirming that TGFB and NOTCH inhibition generates uniform and true hepatocytes from ES cells.

H9-ALB-GFP-let7c derived hepatocytes are mature. A dual marker cell line was made that expresses green fluorescent protein driven by the mature hepatic gene Albumin (ALB) locus along with let7c (ALB-GFP-let7c) by transfecting the construct into H9 cells. The H9-ALB-GFP-let7c hepatocytes were differentiated using a previous protocol (Sengupta et. al. 2014 Toxicological Sciences). H9-ALB-GFO-let7c hepatocytes are as mature as primary human hepatocytes after about 60 day in culture. These ALB-GFP-let 7c hepatocytes were sorted for GFP expression after 57 days and analyzed for hepatocyte markers, as shown in Table 6. As demonstrated in Table 6, these hepatocytes are mature after about 60 days in culture.

TABLE 6 hepatocyte markers in matured cell lines.

| gene | Hep_G2_ND | PHH_7_uncultured | PHH_8_uncultured | PHH_9_uncultured | ALB + ve dual cl cells | alb + ve let7c cells |
|---|---|---|---|---|---|---|
| AFP | 2441.83 | 53.76 | 34.89 | 0.92 | 73108.74 | 11.59 |
| ALB | 7031.37 | 119592.34 | 89417.69 | 36345.64 | 4332 | 1609.35 |
| HNF4A | 58.94 | 16.48 | 24.15 | 20.66 | 21.45 | 10.39 |
| CYP3A4 | 0.1 | 1702.86 | 956.25 | 182.59 | 0.25 | 2.52 |
| CYP3A7 | 0.99 | 190.77 | 50.22 | 0.38 | 9.5 | 1.2 |
| CYP2C9 | 0 | 801.76 | 874.78 | 116.69 | 1 | 43.77 |
| CYP2D6 | 3.29 | 81.68 | 74.66 | 26.63 | 2.1 | 23.33 |
| UGT1A1 | 8.08 | 89.95 | 136.74 | 28.52 | 0.33 | 9.98 |
| UGT1A9 | 0 | 59.96 | 82.38 | 8.45 | 0 | 11.47 |
| UGT1A6 | 0.53 | 241.16 | 266.08 | 181.35 | 0 | 73.14 |

Figure 9C:
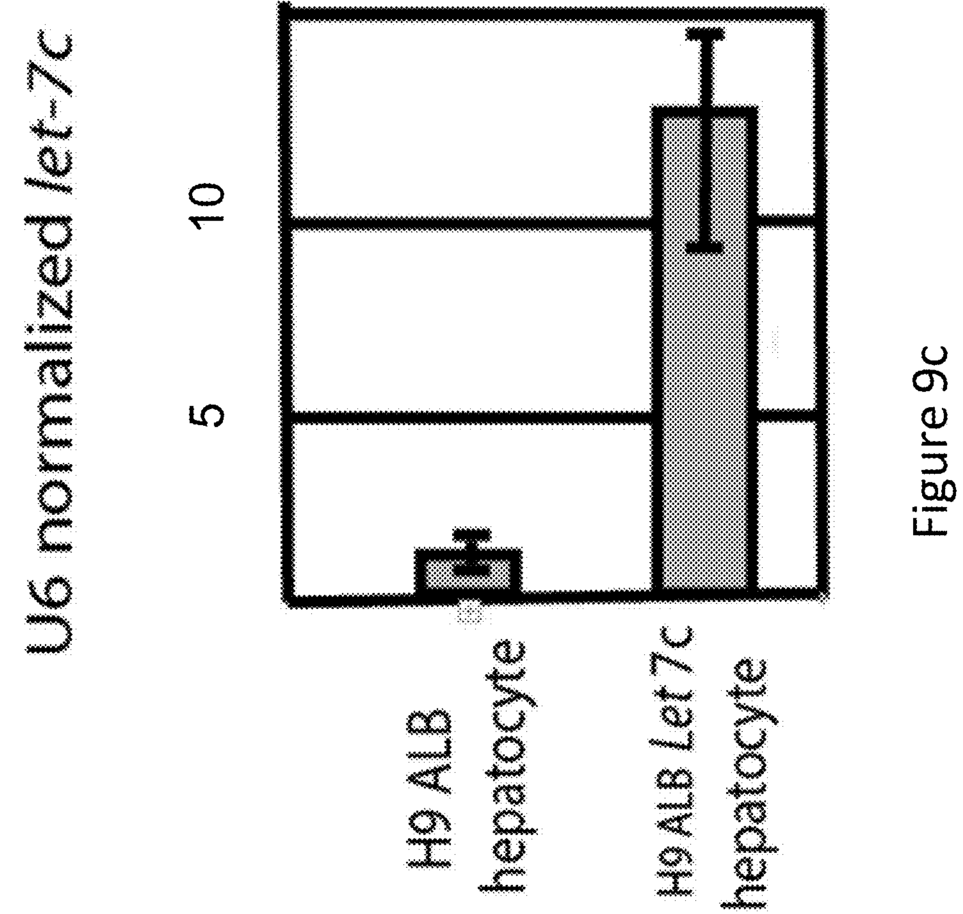
FIG. 9*c*.

ALB-GFP-let 7c hepatocytes are mature. ALB-GFP-let7c transduced cell clones show close correlation to primary hepatocyte cells by transcriptome-wide and liver specific genes when compared to primary human hepatocytes (HPP) as demonstrated in FIGS. 9A and 9B. FIGS. 9A and B were generated by performing Spearman's correlation analysis using the RNA-Seq data from the experiment described above.

Hepatocytes derived from two clones, H9-ALB-GFP/AFP-Tomato (also called the dual clone 1, described in FIG. 3) and H9-ALB-GFP-let7c were differentiated using the Sengupta et al. 2014 Toxicological Sciences protocol. The albumin expressing GFP positive cells we sorted by FACS after differentiation of both lines to hepatocytes. Table 7 shows the comparison of fetal HepG2s, PHHs (primary uncultured adult human hepatocytes from multiple donors), the ALB-GFP positive ES derived hepatocytes and the ALB-GFP positive let7c expressing ES derived hepatocytes. There was a ~8-fold upregulation of let7c as measured by QPCR (See FIG. 9*c*) in the let7c clone.

Longer Activin a Treatment Generates Advanced Hepatocytes from ES Cells that Express Higher Levels of Phase I and Phase II Enzymes.

Figure 4:
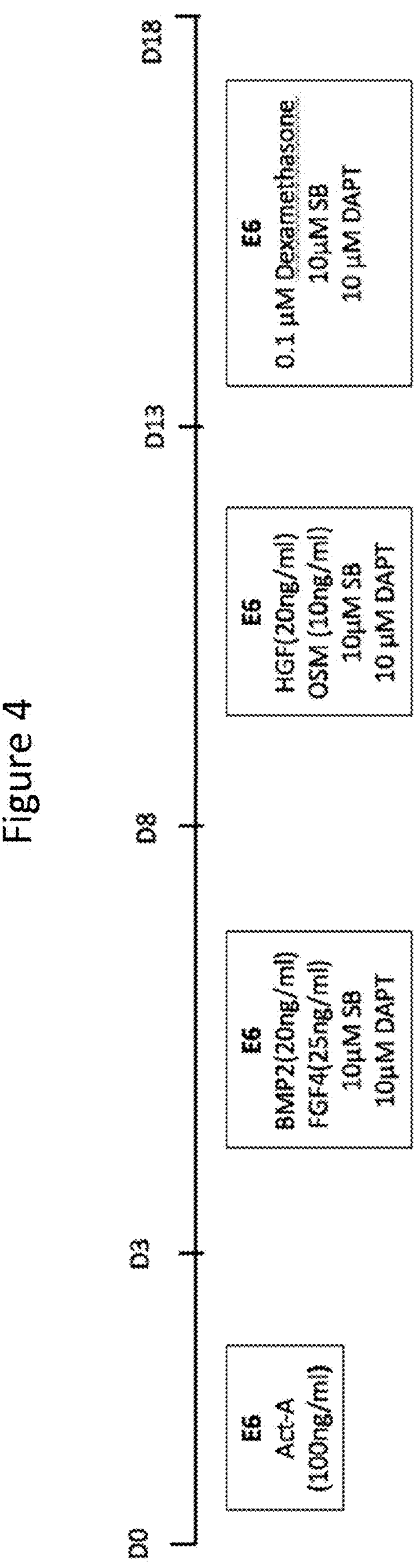
FIG. 4. Schematic of the differentiation protocol used to generate pure hepatocytes from human ES cells.

The H9-ALB-GFP/AFP-Tomato (dual clone 1) were differentiated to hepatocytes using the protocol depicted in FIG. 4. Either 3 day or 18 days of Activin A treatment was used with the rest of the protocol being the same. The cells were not sorted and differentiated for 18 and 33 days (for 3 and 18 day DE respectively).

The gene expression of phase I and phase II enzymes is shown in Table 7.

TABLE 7

Gene expression of after culturing ES cells with Activing A for 3 or 18 days.

| Gene | Dual_cl1_ hepatocyte_ 3_day_DE | Dual_clone_ 1_hep_18_ day_DE | phh_5_ uncultured |
|---|---|---|---|
| ALB | 600.43 | 5129.36 | 65101.07 |
| AFP | 1663.62 | 8635.2 | 8.14 |
| CYP1A1 | 23.85 | 80.48 | 2.7 |
| CYP3A4 | 0.92 | 33.64 | 1115.38 |
| CYP2C9 | 2.26 | 76.46 | 923.74 |
| CYP2D6 | 2.24 | 3.51 | 232.3 |
| CYP2E1 | 0 | 0.4 | 2778.03 |
| UGT1A1 | 3.86 | 66.36 | 159.02 |
| UGT1A6 | 1.75 | 23.94 | 161.13 |

Discussion

Here we report our discovery that TGFB and NOTCH pathways impede differentiation of ES cells towards the hepatic lineage, and showed that inhibition of TGF-beta and NOTCH leads to generation of uniform and true hepatocytes from ES cells that express hepatocyte specific markers.

TGFB had previously been shown to direct cells towards the pancreatic fate over hepatic one during differentiation (Reference 3). NOTCH had also been implicated in controlling fate decision between hepatocyte and cholangiocyte, favoring the cholangiocytic lineage (Reference 4). We also increased the Activin A treatment from 3 to 7 days, as longer treatment by Activin A has been shown to lead to higher number of cells expressing definitive endoderm markers as well as specify hepatic fate more efficiently (Reference 5). We found that increasing the treatment with Activin A to up to 18 days generates advanced hepatocytes from ES cells that express all major phase I and phase II enzymes listed in Table 7.

Generation of pure hepatocytes from pluripotent stem cells will allow drug development and study of inherited liver diseases using disease-specific iPS-derived hepatocytes. This also opens the possibility for cell transplantation in the clinic with patient specific iPS-derived hepatocytes that would circumvent immunosuppression.

Materials and Methods

Hepatocyte Differentiation

ES cells were cultured in E8 medium (Reference 2) and were differentiated to hepatocytes following a previously published protocol (Reference 1) with modifications. Briefly, at approximately 50% confluency the ES cells were singularized by accutase and seeded on matrigel coated plate in E6 medium containing 100 ng/ml Activin A (Sigma). They were cultured in the Activin A medium for seven days. From day 8 to day 12 the cells were treated with 25 ng/ml FGF4 (R&D Systems) along with 20 ng/ml BMP2 in E6. During days 13 through 17 the cells were treated with 20 ng/ml HGF (R&D Systems) and 10 ng/ml Oncostatin M (R&D Systems) in E6. Finally, the cells were cultured in E6 containing 0.1 μM Dexamethasone (Sigma) from day 18 to day 22. From day 8 onwards, SB431542 and DAPT were added to the medium to inhibit TGFB and NOTCH respectively at 10 μM final concentration.

Flow Cytometric Analysis

H1 and H9 derived hepatocytes were immunostained for ASGR1 by first fixation at −80° C. for 20 mins in 80% methanol and 20% blocking solution (made up of 20% FBS in PBS). The cells were then washed and blocked at room temp for 1 hour in blocking solution. After blocking, 20 μls of primary antibody (FITC conjugated ASGR1, SC-52623, Santa Cruz Biotech) was added to the cells in 1 ml blocking solution and shaken overnight at 4° C. Next the cells were washed twice in blocking buffer and analyzed by flow cytometry.

References for Example 2

Reference 1. Aggregate culture of human embryonic stem cell-derived hepatocytes in suspension are an improved in vitro model for drug metabolism and toxicity testing. (2014). Sengupta S, Johnson B P, Swanson S A, Stewart R, Bradfield C A, Thomson J A. *Toxicol Sci.* 140(1): 236-45.

Reference 2. Chemically defined conditions for human iPSC derivation and culture. (2011). Chen G, Gulbranson D R, Hou Z, Bolin J M, Ruotti V, Probasco M D, Smuga-Otto K, Howden S E, Diol N R, Propson N E, Wagner R, Lee G O, Antosiewicz-Bourget J, Teng J M, Thomson J A. *Nat Methods.* 8(5): 424-9.

Reference 3. Efficient endoderm induction from human pluripotent stem cells by logically directing signals controlling lineage bifurcations. (2014). Loh K M, Ang L T, Zhang J, Kumar V, Ang J, Auyeong J Q, Lee K L, Choo S H, Lim C Y, Nichane M, Tan J, Noghabi M S, Azzola L, Ng E S, Durruthy-Durruthy J, Sebastiano V, Poellinger L, Elefanty A G, Stanley E G, Chen Q, Prabhakar S, Weissman I L, Lim B. *Cell Stem Cell.* 14(2): 237-52.

Reference 4. Notch is the key factor in the process of fetal liver stem/progenitor cells differentiation into hepatocytes. (2012). Wang T, You N, Tao K, Wang X, Zhao G, Xia N, Li N, Tang L, Liu W, Dou K. *Dev Growth Differ.* 54(5): 605-17.

Reference 5. New markers for tracking endoderm induction and hepatocyte differentiation from human pluripotent stem cells. (2015). Holtzinger A, Streeter P R, Sarangi F, Hillborn S, Niapour M, Ogawa S, Keller G. *Development.* 142(24): 4253-65.

Example 3: Maturation of a Hepatic Cell Line, HepG2, for Drug Toxicity Testing

Example 3: Maturation of a Hepatic Cell Line, HepG2, for Drug Toxicity Testing

This Example demonstrates the use of the present methods to mature the hepatic cell line HepG2 and also to prevent the loss of mature function of cultured primary hepatocytes. These cells, in turn, then can be used for drug toxicity testing as demonstrated for acetometophen.

Given the difficulties in obtaining and maintaining primary human hepatocytes, attempts have been made to use transformed hepatic cell lines such as the human hepatoma cell line HepG2 (Knowles et al., 1980) for drug testing (Donato et al., 2008). While such cell lines have the advantage of being easy to culture and expand, their use in in vitro liver modeling is limited as they poorly metabolize xenobiotics due to low levels or lack of many phase I and II enzymes and drug transporters and are refractory to infection by hepatotropic viruses (Gerets et al., 2012).

In this Example, the Inventors demonstrate that mitogen activated protein kinase (MAPK) pathway genes are upregulated in cultured PHHs concomitant with downregulation of xenobiotic metabolism-associated genes. Inhibiting of the MAPK pathway by small molecules helps maintain the expression of hepatic genes that are normally reduced or lost during culture, and MAPK inhibition upregulates these same genes in HepG2 cells. In HepG2 cells, MAPK inhibition upregulates the metabolism of the classic hepatotoxicant acetaminophen and induces other liver-specific genes such as the hepatitis B virus (HBV) and hepatitis C virus (HCV) receptors.

Materials and Methods

Primary Hepatocytes. Multiple batches of cryopreserved induction qualified human hepatocytes (each batch being from one donor) were purchased from Life Technologies and cultured on Matrigel coated plates in hepatocyte growth medium (PromoCell). For dedifferentiation studies, hepatocytes from batches Hu4260, Hu8135, Hu4279 and Hu8137 were used after mixing equal number of live cells. For small molecule treatments, batch Hu4260 was used. Mouse hepatocytes were isolated from Black 6 mice livers by perfusion following standard protocol and cultured on Matrigel coated plates in hepatocyte growth medium (Promocell).

Gene Expression Analysis. Total RNA were isolated using RNAeasy Plus Kit (Qiagen) following manufacturers protocol and qualified with the Life Technologies Qubit fluorometer and Agilent Bioanalyzer. Indexed cDNA libraries were prepared with the Ligation Mediated Sequencing (LM-Seq) protocol (Hou et al., 2015) for all samples except uncultured PHH (batch 4260) and PHH mixtures that were uncultured and cultured for 24 hours, which were prepared using TruSeq kit (Illumina). Final indexed cDNA libraries were pooled and sequenced on an Illumina HiSeq 2500. Base-calling and demultiplexing were performed using Casava (v1.8.2). Sequences were filtered and trimmed to remove low quality reads, adapters, and other sequencing artifacts. The remaining reads were aligned to a reference database comprising only RefSeq—validated transcripts (i.e., assigned an "NM_" accession). Mouse samples were aligned to the mm10 assembly, and human samples were aligned to the hg19 assembly. Bowtie (v 0.12.9) was used for alignment, allowing two mismatches in a 28 bp seed (Langmead et al., 2009). Reads with more than 200 alignments were excluded from further analysis. RSEM (v1.2.3) was used to estimate relative gene expression levels (transcripts per million or "TPM") (Li and Dewey, 2011). All RNA-seq results have been deposited at NCBI's GEO under Accession No: GSE94353.

Acetaminophen metabolism testing. Samples for LC/MS/MS analysis were processed by solid-phase extraction, and calibrant curves (7 points) for all compounds were generated by spiking standards (Sigma) in E6 media and processed in parallel with samples. An internal standard of deuterated naproxen was included for all analytes. Samples were run on a 0.2×100 mm Cortecs C18 column (Waters Corporation, Milford MA) using a Waters Acquity UPLC system coupled to an AB/Sciex Q-Trap 5500 hybrid triple quadrupole instrument (Framingham MA). Analytes were detected using multiple-reaction-monitoring with three transitions for each compound being monitored. Each sample was analyzed in triplicate with blanks between each sample analysis. Quantitation was based on area under the curve of the analyte relative to the internal standard and was modeled with a quadratic fit with 1/x weighting using the MultiQuant software (Sciex, Framingham MA). Calibrator points that gave calculated concentrations differing by >15% from the expected values were excluded from the model. Average calculated concentrations for each analyte are reported. Samples that had percent relative standard deviations >15% were not considered valid. Background was determined by measuring metabolites in media incubated with acetaminophen only for 1 hour and any samples below background were considered nil. Parent and fragment ion masses for MRM analysis of metabolites of acetaminophen were as follows: APAP-Sulfate: parent 230 (−), fragment 150, 107, 80; APAP-Glucuronide: parent 328.1 (+), fragment 152, 141, 65 and APAP-Glutathione: parent 457.1 (+), fragment 328, 182, 140.

CYP functional assay. HepG2 cells cultured in DMEM/F12 with 10% FBS were incubated with DMSO or U0126 for 72 hours. CYP2C9 and 3A4 metabolism were measured using CYP450 Glo assay (Promega). Substrates were added to the media and incubated for 72 hours and the amount of metabolite generated were measured by adding the detection reagent and quantifying the luminescence in a Tecan plate reader. Background was measured by incubating the substrates for 72 hours in the same media without cells.

Results

Figure 10B:
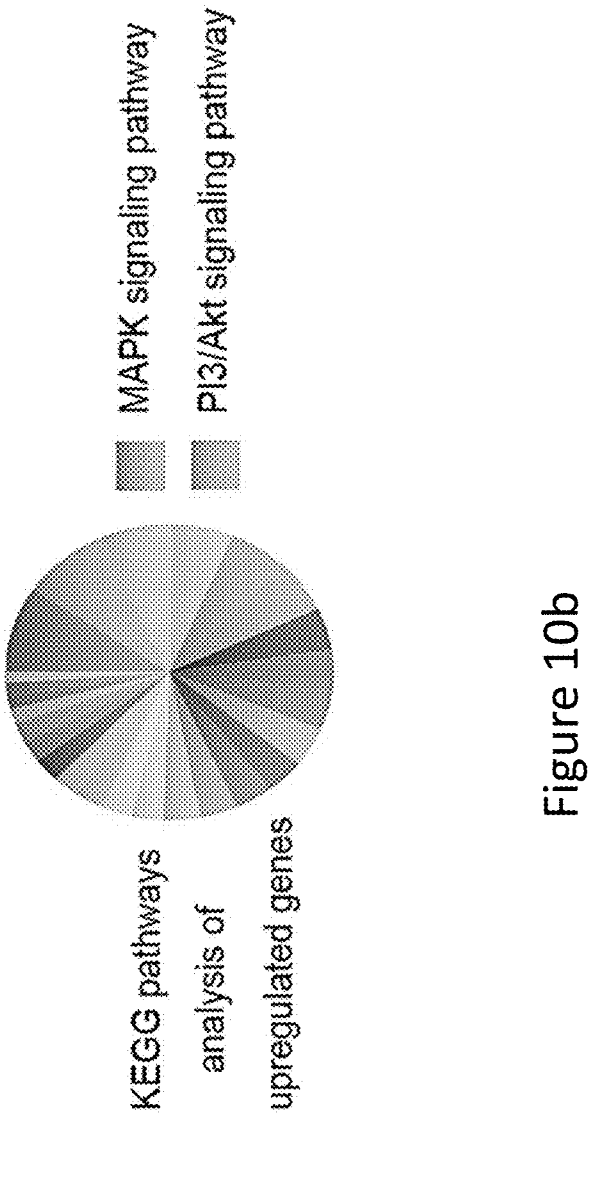
FIG. 10*b*. KEGG pathway analysis of genes upregulated during culture of PHHs. i) MAPK pathway genes show the highest overrepresentation among the upregulated genes among all cell signaling pathways as identified by KEGG followed by PI3/Akt ii) MAPK pathway showing a significant portion of its genes to be upregulated (highlighted in red) during culture including ERK (MAPK1) and MEK1 (MAP2K1), central players of this pathway.
Figure 10B:
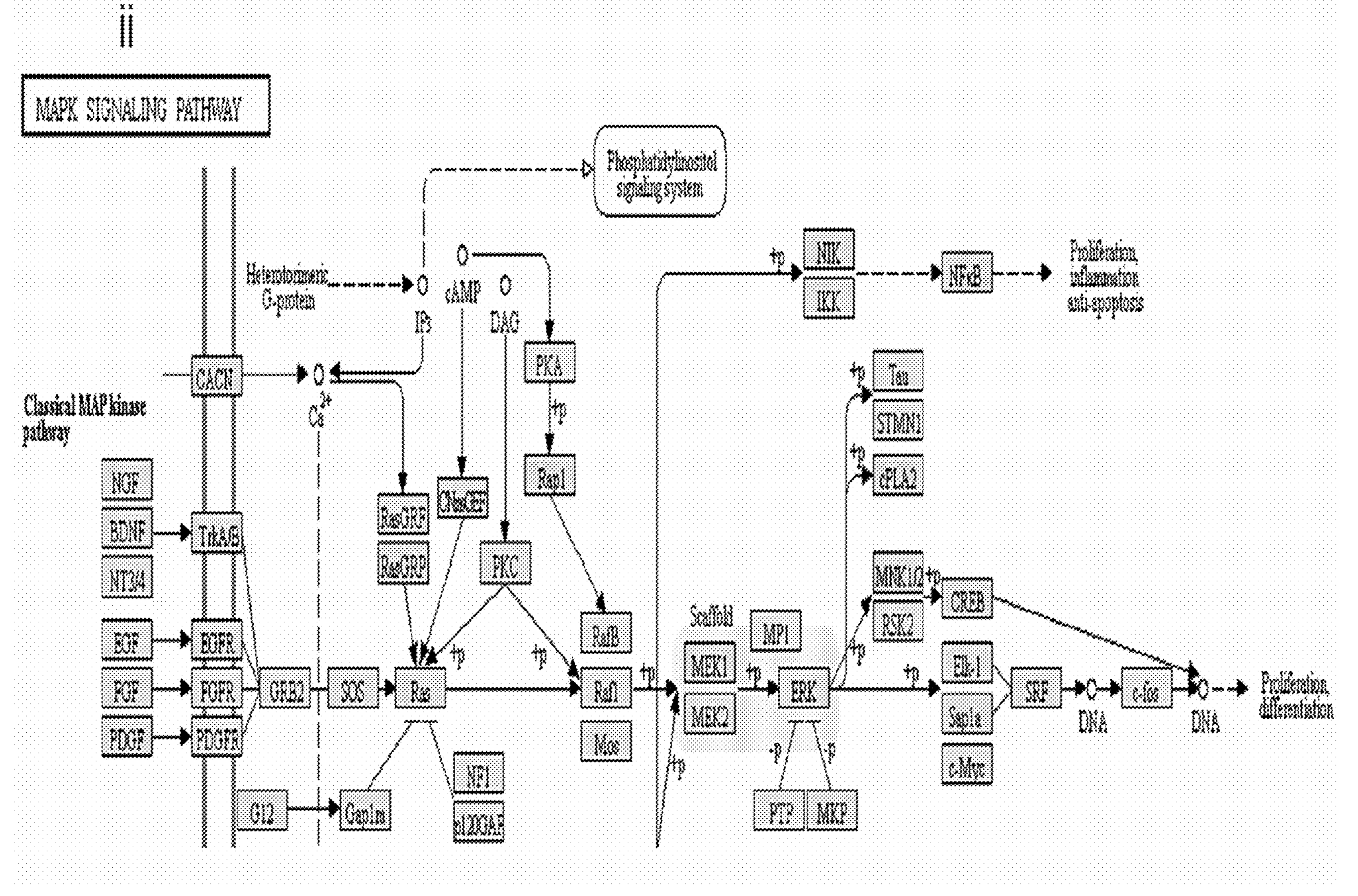

MAPKs are upregulated during hepatocyte dedifferentiation. RNA-Seq was performed on fresh PHHs and on PHHs after 24 hours of culture that were isolated from four separate donors (Supplementary Table 1 in U.S. Application No. 62/531,424, incorporated by reference in its entirety). Genes which were upregulated at least 5-fold to at least 10 transcripts per million (TPM) and downregulated at least 5-fold from a minimum of 10 TPM were considered differentially expressed. There was a higher number of genes that were upregulated (2328) compared to those that were downregulated (265) during 24 hours of culture. To understand the function of genes that changed expression during dedifferentiation, we classified them by their protein categories in INTERPRO database (Mitchell et al., 2015) using DAVID 6.7 (Huang da et al., 2009a, b), which mapped more than 90% of genes in both upregulated and downregulated categories. The three most statistically enriched clusters of downregulated genes were xenobiotic metabolism-associated genes (cytochrome P450s or CYP450s/CYPs), dehydrogenases, and blood plasma proteins (alpha 2-macroglobulins) (FIG. 10 *ai*). The three most enriched group of genes in the upregulated category were protein and serine/threonine kinases, WD40 repeats, and GTPases (FIG. 10 *aii*). The top upregulated group, protein and serine/threonine kinases, were dominated by mitogen activated protein kinases (MAPKs) (FIG. 10 aiii).

Signal transduction pathways modulate cellular response to their microenvironment, and, given that hepatocyte differentiation and maturation are associated with their environmental status (i.e., in vivo or ex vivo), pathway analysis by KEGG (Kanehisa and Goto, 2000) (Kanehisa et al., 2016) was used to identify signaling pathways associated with hepatocyte dedifferentiation. KEGG analysis of the upregulated genes again showed MAPK to be the dominant pathway with the most overrepresentation among upregulated genes, followed by the PI3/Akt pathway (FIG. 10 *bi*). The MAPK pathway (FIG. 10 *bii*) shows ERK (MAPK1) and MEK1 (MAP2K1), genes central to this pathway, to be among those upregulated during dedifferentiation (in red boxes).

Figure 11A:
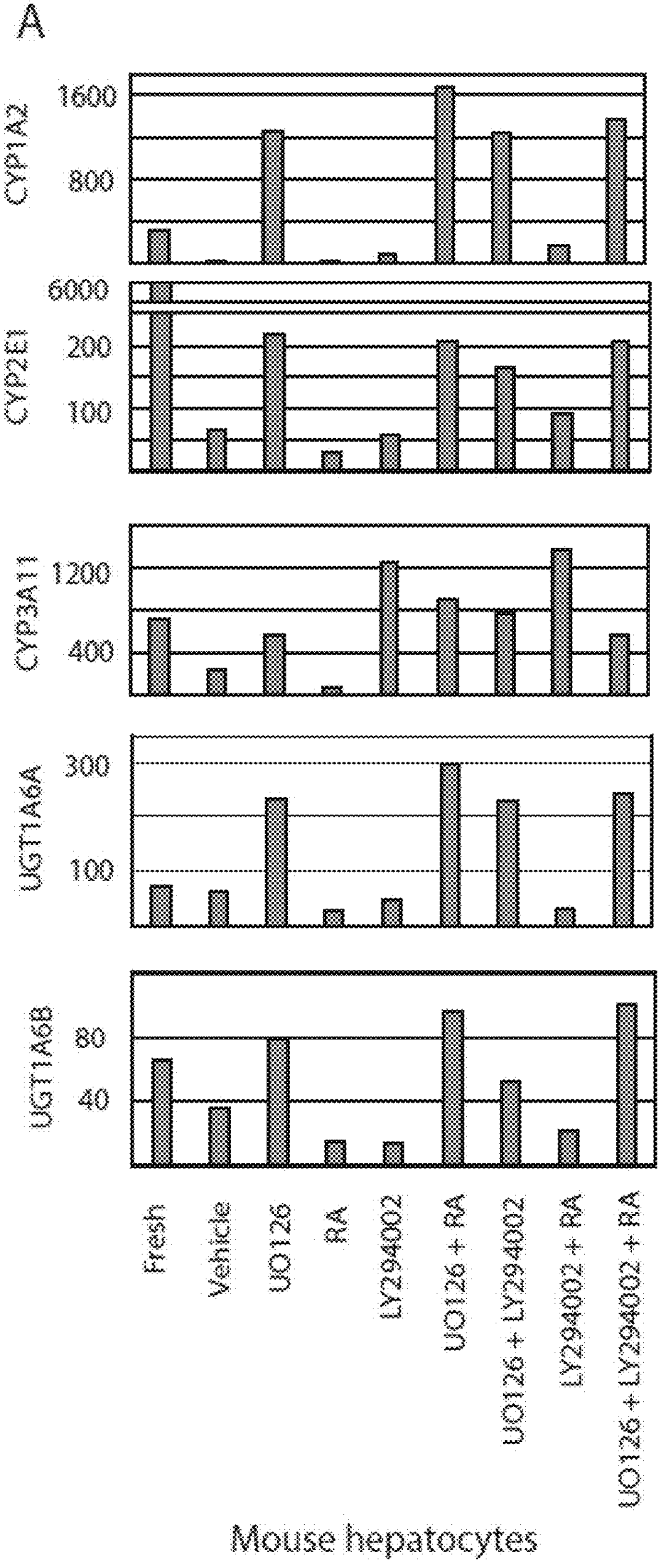
FIG. 11*a*. Effects of mitogen-activated protein kinase (MAPK), PI3/Akt, and mTOR pathways on maintenance of maturity in cultured mouse hepatocytes. MAPK inhibition by U0126 treatment was performed alone or in combination with other inhibitors. MAPK inhibition by U0126 increased expression of metabolic enzymes which were reduced in mouse hepatocytes cultured for 72 hours. Gene expression values are in transcripts parts per million.

MAPK inhibition maintains expression of hepatic genes downregulated in dedifferentiation. The inventors next investigated whether the MAPK and PI3/Akt pathways contributed to the dedifferentiation of hepatocytes. Primary mouse hepatocytes were treated with the MAPK pathway inhibitor U0126 and the PI3 pathway inhibitor LY294002, either individually or in combination, at 10 μM concentrations. Rapamycin was included as a control, which is an inhibitor of the mTOR pathway, a serine/threonine kinase involved in cell signaling not identified as a key pathway in our analysis. The inventors then analyzed the treated hepatocytes, vehicle-treated hepatocytes, and fresh uncultured hepatocytes using RNA-Seq (Supplementary Table 2, in U.S. Application No. 62/531,424, incorporated by reference in its entirety). Hepatocytes treated with the MAPK inhibitor U0126 for 72 hours maintained expression levels of mouse orthologs of important human metabolic enzymes and mouse enzymes similar to human enzymes by substrate specificity (Jiang et al., 2011; Martignoni et al., 2006) at significantly higher levels than untreated control hepatocytes (FIG. 11*a*). One member each from the CYP1, 2, 3, and uridine 5'-diphospho-glucuronosyltransferases (UGT) 1 families were examined and found to lose expression during culture in untreated hepatocytes. In the majority of cases, U0126 increased the mRNA levels to equal to or greater than that which was present in fresh uncultured hepatocytes; the exception being CYP3A11 (equivalent of human CYP3A4), which was increased by the PI3/Akt pathway inhibitor LY294002. Thus, this analysis of MAPK, PI3/Akt, and mTOR pathway inhibition showed U0126 to upregulate metabolic enzymes both by itself and in the presence of other inhibitors.

Figure 11B:
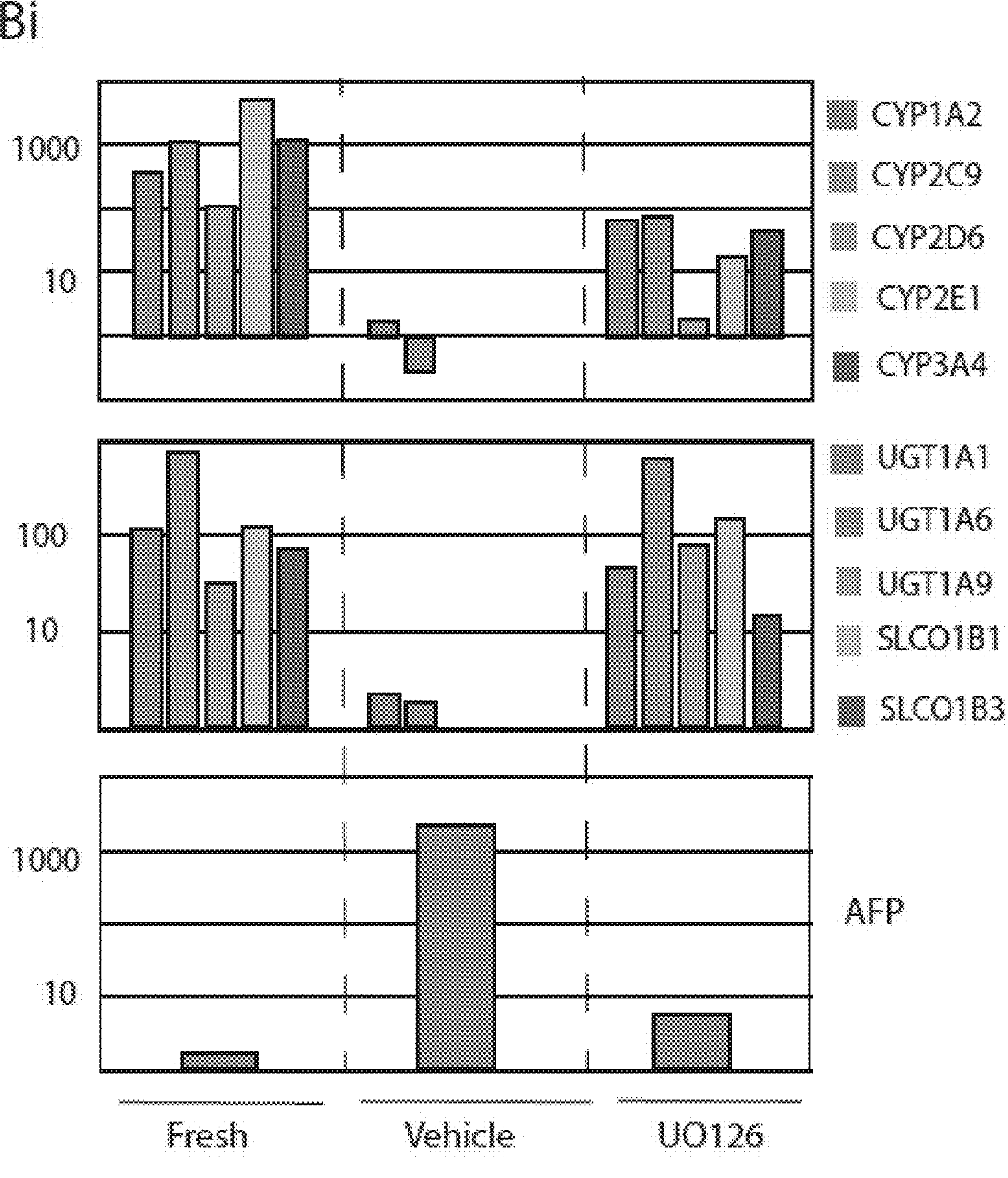
FIG. 11*b*. MAPK inhibition maintains expression of genes involved in drug metabolism (phase I, II, and transporters) that are lost or reduced in primary human hepatocytes (PHHs) cultured for 72 hours and suppresses the fetal marker AFP. i) PHHs treated with U0126 for 72 hours and ii) PHHs treated with PD0325901 for 72 hours. Gene expression values are in transcript parts per million.
Figure 11B:
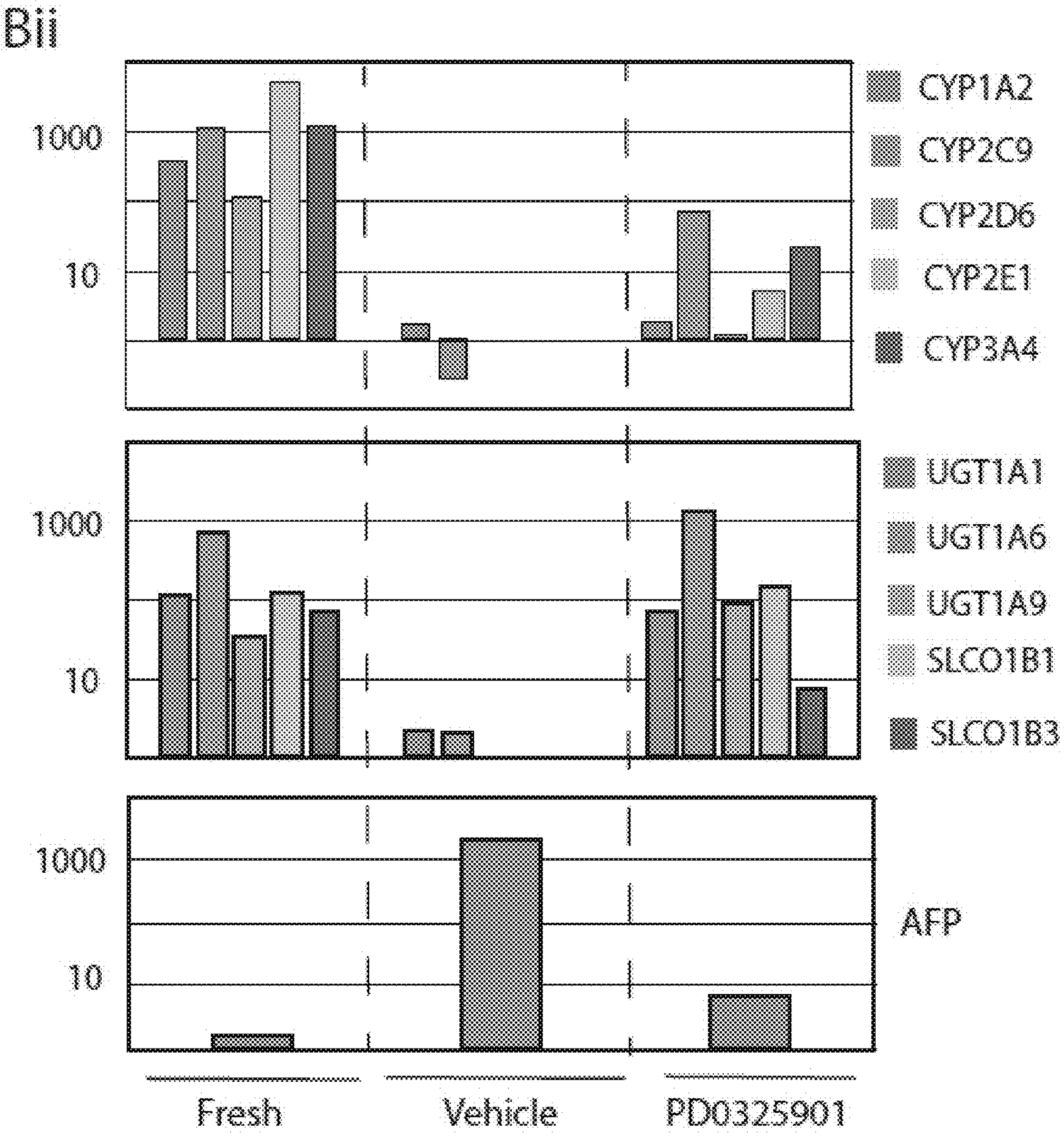

PHHs were cultured with U0126 or vehicle control for 72 hours, then analyzed along with fresh PHHs using RNA-Seq (Supplementary Table 3 in U.S. Application No. 62/531,424, incorporated by reference in its entirety). Key drug metabolic and transporter enzymes (International Transporter et al., 2010) were all maintained at higher levels in U0126 treated cells compared to vehicle control (FIG. 11*bi*). After 72 hours of U0126 treatment, UGTs and transporters were both maintained at levels comparable to levels observed in fresh PHHs and were up to 2 orders of magnitude higher than levels in cultured vehicle control PHHs. CYP P450s levels in U0126 treated PHHs were significantly higher at 72 hours compared to vehicle treated controls but did not achieve levels equal to fresh uncultured PHHs. Concomitant with maintenance of metabolic enzymes by U0126, the upregulation of the fetal marker AFP at 72 hours observed in untreated control cells was reduced by 2 orders of magnitude in U0126 treated cells.

To ascertain that the increase in metabolic enzymes took place through specific MAPK inhibition, PHHs were treated with a second MAPK inhibitor, PD0325901, for 72 hours, followed by RNA-Seq analysis (Supplementary Table 4). We examined the same set of enzymes and transporters and found that PD0325901 mirrored the effect of U0126 in upregulating metabolic enzymes while downregulating AFP, demonstrating MAPKs specific role in hepatic maturity (FIG. 11*bii*). Also of note, the HCV receptor was upregulated in U0126 and PD0325901 treated PHHs, and the HBV receptor was upregulated in PD0325901 treated PHHs (Supplementary Tables 3 and 4 in U.S. Application No. 62/531,424, incorporated by reference in its entirety).

Figure 12A:
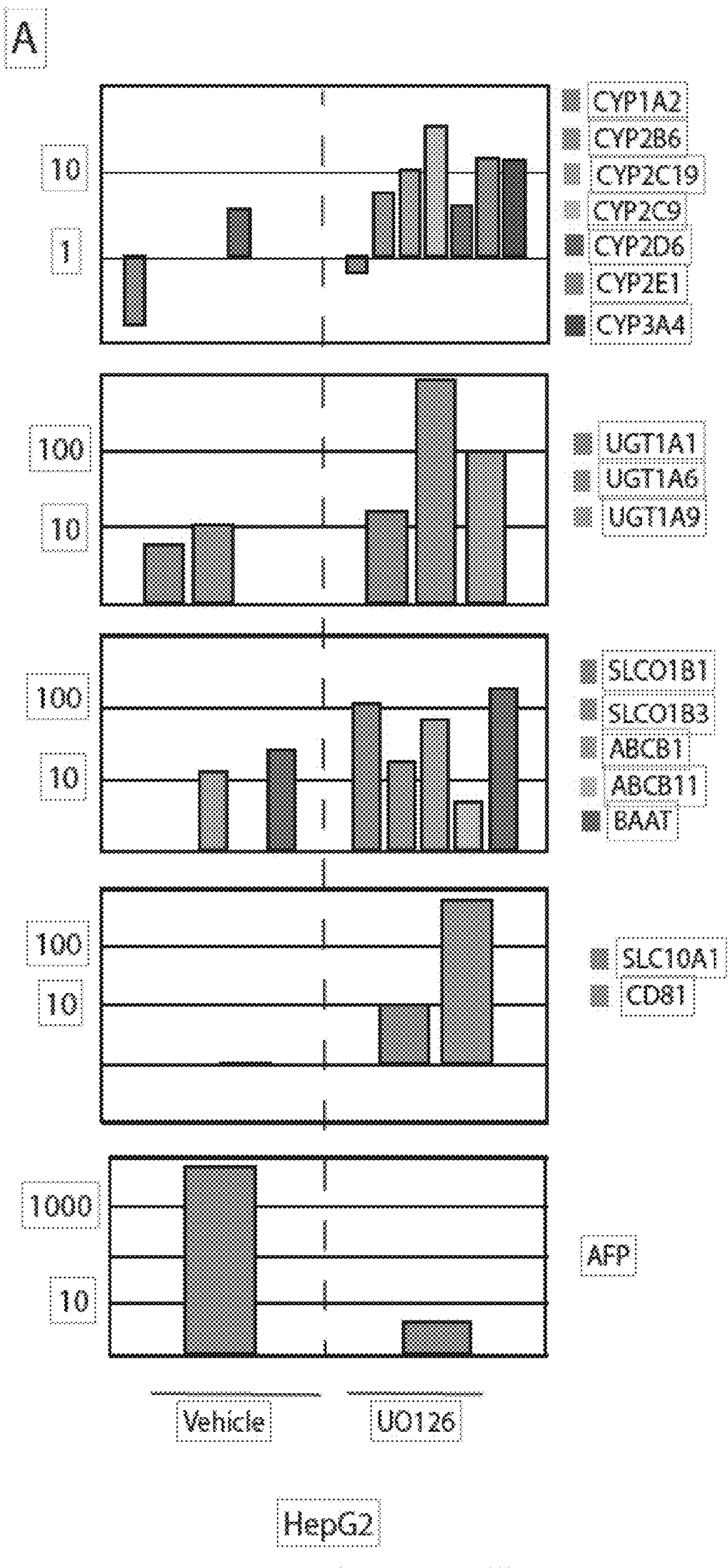
FIG. 12*a*. U0126 matures HepG2s. HepG2s treated with U0126 for 72 hours upregulates expression of drug metabolizing enzymes, transporters, hepatitis B virus (SLC10A1) receptor, and hepatitis C virus (CD81) receptor, and downregulates the fetal marker AFP. Gene expression values are in transcript parts per million.
Figure 12B:
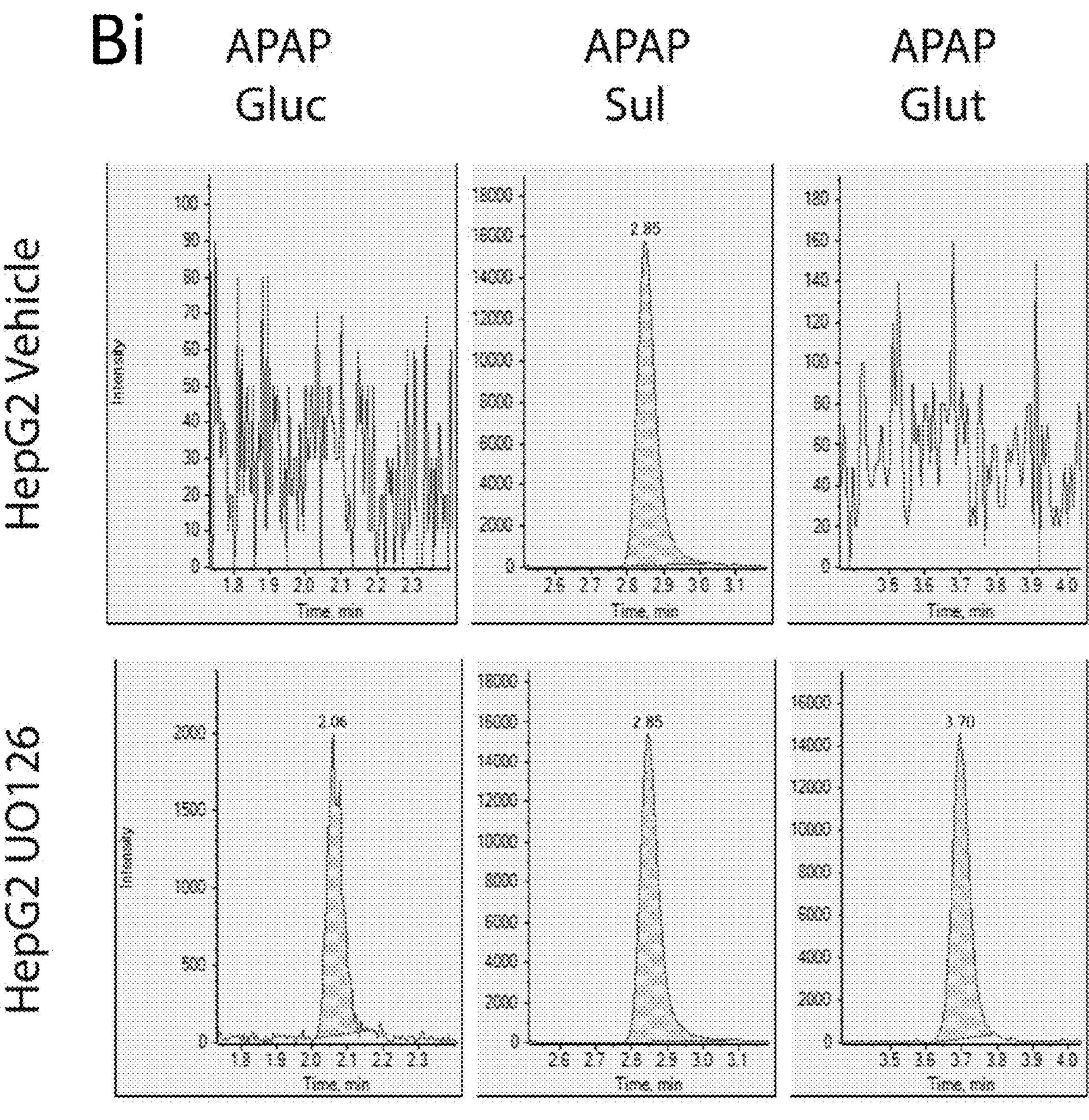
FIG. 12*b*. LC/MS/MS analysis of acetaminophen (APAP) metabolism. i) Extracted ion chromatograms of the three major metabolites of APAP from vehicle or U0126 treated HepG2 cells. Vehicle treated HepG2s do not form APAP-glucuronidates or APAP-glutathione. ii) U0126 treated HepG2s metabolize acetaminophen to its three major metabolites at the same rate per hour as fresh uncultured adult primary human hepatocytes.
Figure 12B:
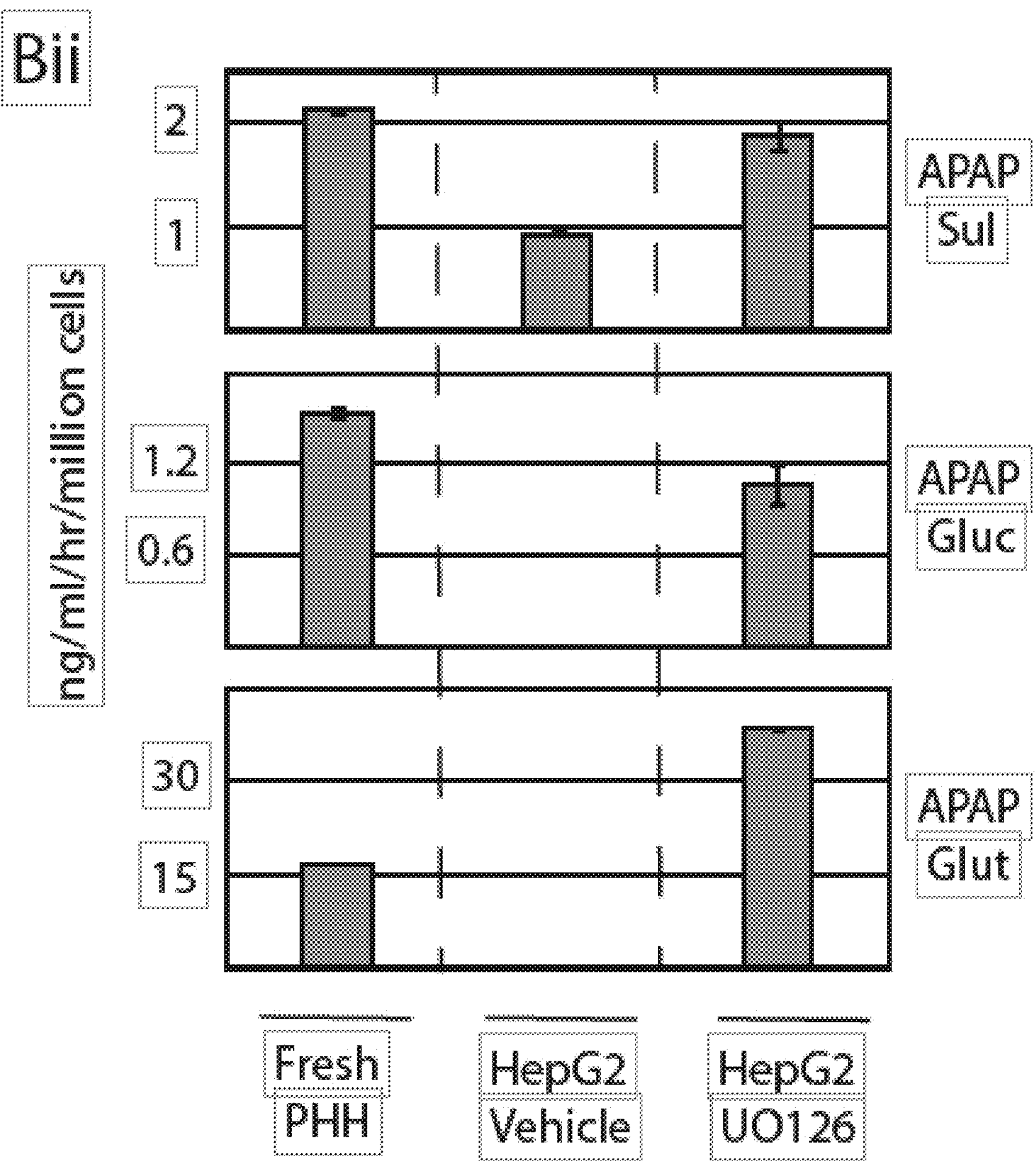

MAPK inhibition matures HepG2 cells. The inventors next explored whether MAPK inhibition would improve the mature function of HepG2 cells. HepG2 cells were treated with U0126 or vehicle control for 72 hours. RNA-Seq (Supplementary Table 5 in U.S. Application No. 62/531,424, incorporated by reference in its entirety) analysis showed that U0126 upregulated phase I and phase II enzymes and drug transporters, as well as downregulated AFP (FIG. 12*a*). To test whether the upregulation of metabolic genes at the mRNA level translated into functional metabolic improvement, acetaminophen (APAP) metabolism was assessed by LC/MS/MS. U0126 treated HepG2 cells and control HepG2 cells were cultured for 72 hours and exposed to 10 uM APAP for 1 hour in E6 basal media (Chen et al., 2011). U0126 treatment of HepG2 cells increased formation of APAP-sulphate and induced the formation of APAP-glucuronide and APAP-glutathione (FIG. 12*b*). Similar to a previous study, glucuronidation and APAP-glutathione formation was undetectable in untreated HepG2 cells (FIG. 12*bi*) (Sengupta et al., 2014). Importantly, all the APAP metabolites in U0126 treated HepG2 cells were formed at a comparable rate to mature adult PHHs (FIG. 12*bii*).

Figure 12C:
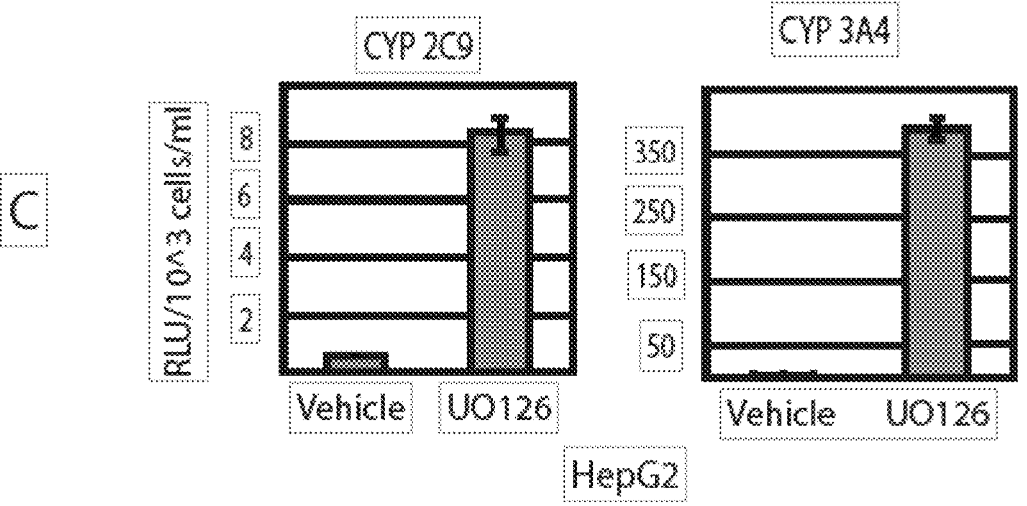
FIG. 12*c*. CYP2C9 and 3A4 activities are 10- and 30-fold higher in U0126 treated HepG2 cells.

The activity of two important drug metabolizing enzymes, CYP2C9 and CYP3A4, were analyzed in HepG2 cells treated with vehicle control or U0126 for 72 hours using a luminescence assay. U0126 upregulated CYP2C9 and CYP3A4 activity by 10- and 30-fold respectively as measured by the generation of luminescent metabolites confirming U0126 treatment to improve the functionality of HepG2 cells (FIG. 12*c*).

Interestingly, U0126 also induced the expression of both HBV and HCV receptors, making HepG2s potentially susceptible to infection and useful for viral studies (FIG. 12*a*). Transformed cell lines, including HepG2s, are refractory to infection by hepatotropic viruses. A cell line which allows productive infection, HepaRG, not only requires extended treatment with dimethyl sulfoxide to achieve maturation, but less than 10% of cells are infectable by HBV even with high titres of inoculum, which is sufficient for infection of 100% of PHHs in vitro (Schulze et al., 2012). Expression of SLC10A1 and CD81, HBV and HCV receptors, respectively, was rapidly induced in HepG2s by U0126 treatment. Use of HepG2s to support replication of HBV or HCV would provide a simple, readily accessible system for studying HBV and HCV and for developing antivirals.

Discussion

This Example demonstrates that inhibition of the MAPK signaling pathway reduces the loss of mature function of PHHs in culture and improves the mature function of HepG2 cells which normally exhibit only limited hepatic metabolic activity. This simple method to maintain and generate more functional hepatocytes improves the availability of hepatic cells for drug development and toxicity testing. After 72 hours of culture, phase II enzymes (i.e., UGTs) and drug transporters (SLCO1B1, SLCO1B3) showed an increase of up to 2 orders of magnitude in both PHHs and HepG2 cells with MAPK inhibition, and phase I enzymes (i.e., CYP P450s) showed an increase of up to 1 order of magnitude.

Other members of phase II metabolism also showed a significant increase, including glutathione transferases (i.e., GST1, GSTP1), in both HepG2s and PHHs. In addition, acetyltransferases (i.e., NAT1, NAT2), but not sulphotransferases (i.e., SULT1A1, 1A2) increased in HepG2s with MAPK inhibition (Supplementary Table 5 in U.S. Application No. 62/531,424, incorporated by reference in its entirety). The biggest increase by MAPK inhibition was in the liver N-methyltransferase NNMT, which was not detected in either HepG2s or 72 hour cultured PHHs but was upregulated to TPM of 3 digits in both cell types (Supplementary Table 4 and 5 in U.S. Application No. 62/531,424, incorporated by reference in its entirety). Both U0126 and PD0325901 upregulated NNMT in PHHs to within 10-fold of expression levels found in uncultured PHHs. Metabolic genes were maintained at higher levels in freshly isolated mouse primary hepatocytes compared to PHHs possibly due to superior quality of the cells, allowing higher confluency in culture leading to better enzymatic expression.

Although many liver specific genes, such as liver specific cytokeratins (KRT8, 18), were upregulated or preserved by MAPK inhibition, bile acid synthesis genes (BAAT), blood plasma proteins (i.e., ORM1, 2), liver specific apolipoproteins (i.e., APOA1, APOH), alpha 1 antitrypsin and alcohol dehydrogenase (i.e., ADH4) did not show any upregulation. In our study, U0126 treatment also did not significantly change the expression (>3-fold) of hepatic nuclear receptors (i.e., CAR, FXR, LXR, PPAR, PXR, RAR) in either HepG2 cells or PHHs.

In addition to improving metabolic function of HepG2 cells, the inventors found that MAPK inhibition induced the expression of HBV and HCV viral receptors. HBV and HCV studies have historically been hampered by the lack of a simple culture system for maintaining replication competent human hepatocytes. Recently, human pluripotent stem cell derived hepatocytes have been shown to allow infection but require differentiation and purification, adding considerably to the expense (Schwartz et al., 2012; Shlomai et al., 2014). HepaRG cells also require a long maturation period in culture to be receptive to infection and show less than 1/10$^{th}$ of the infectivity by HBV compared to PHHs in culture (Schulze et al., 2012). If U0126 treated HepG2 cells do support robust HBV or HCV replication, it could provide a readily available, simple system for studying these viruses.

The methods described herein regarding hepatocyte maturation with MAPK inhibitors can be used to make cell cultures for use in drug development and toxicity testing.

For example, the methods of the present invention may be able to be used for the treatment of hepatocellular cancer. Similar to other tumor types, with progression, hepatocellular carcinoma becomes increasingly dedifferentiated with a concomitant increase in malignancy. Cancer therapies have historically focused on killing malignant cells, but an alternative strategy would be to drive undifferentiated, proliferative cancer cells to a more differentiated, quiescent state. The ability of MAPK inhibitors to differentiate undifferentiated hepatocytes may be a method to reduce tumor progression.

Example 4: Screen Identifying Compounds that Play a Role in Hepatocyte Maturation A robotic screen was performed to determine compounds that increase expression of albumin in hepatocytes as an indicator that the compounds play a role in hepatocyte maturation. 1200 compounds were screened and 400 compounds analyzed for their effects on hepatocytes with regard to the levels of albumin and fetal marker AFP. Out of the screen, Stauprimide, a c-MYC inhibitor was identified which increased expression of albumin, but did not increase expression of AFB.

The effects of Stauprimide in maturation of ES-derived hepatocytes was validated by RNA-Seq as described above. Briefly, the H9-ALB-GFP/AFP-Tomato (dual clone 1) were differentiated to a pure population of hepatocytes by CDI (Madison, WI) and treated with Stauprimide for 72 hours. Cells were then analyzed by RNA-Seq, and the results are shown in Table 8 below which demonstrates Stauprimide increases mature hepatic genes. Thus, Stauprimide is able to increase expression of mature hepatocyte genes and reduce the expression of the fetal marker AFP.

TABLE 8

RNA-Seq data from hepatocytes treated with Stauprimide

| Gene | DUal_clone_1_ CDI_DMSO_ 72_hrs | DUal_clone_1_ CDI_Stauprimide_ 72_hrs |
|---|---|---|
| ALB | 9312.65 | 8513.48 |
| AFP | 3122.33 | 2485.61 |
| UGT1A9 | 0 | 47.42 |
| UGT1A1 | 423.99 | 322.35 |
| UGT1A6 | 132.84 | 411.32 |
| CYP2C9 | 0.83 | 19.63 |
| CYP2D6 | 0 | 0 |
| CYP2E1 | 13.55 | 9.6 |
| CYP1A1 | 7.64 | 47.04 |
| HNF4A | 14.78 | 25.97 |
| ADH4 | 0 | 12.82 |
| BAAT | 7.09 | 10.4 |
| SERPINC1 | 20.89 | 42.45 |
| SERPINA1 | 7562.18 | 10030.14 |

As such, Stauprimide, like the MAPK inhibitor U0126 can be used to not only mature immature hepatocytes but to maintain the maturity of hepatocytes in culture.

Each publication, patent, and patent publication cited in this disclosure is incorporated in reference herein in its entirety. The present invention is not intended to be limited to the foregoing examples, but encompasses all such modifications and variations as come within the scope of the appended claims.

The invention claimed is:

1. A method of expressing or inducing expression of one or more mature hepatic gene(s) or maintaining expression thereof in a human hepatocyte, the method comprising:
- culturing the human hepatocyte with at least one inhibitor of mitogen activating protein kinase (MAPK),
- wherein the one or more mature hepatic gene(s) are Bile Acid-CoA:Amino Acid N-Acyltransferase (BAAT), Solute Carrier Organic Anion Transporter Family Member 1B1 (SLCO1B1), Cytochrome P450 Family 1 Subfamily B Member 1 (CYP1B1), Cytochrome P450 Family 2 Subfamily C Member 18 (CYP2C18), UDP Glucuronosyltransferase Family 1 Member A6 (UGTIA6), UDP-glucuronosyltransferase 1-9 (UGT1A9), and Cluster of Differentiation 81 (CD81); and
- wherein the cultured human hepatocyte expresses the one or more mature hepatic gene(s) for at least 72 hours at an expression level that is at least 70% the expression level of the same gene(s) in fresh primary hepatocytes.

2. The method of claim 1, wherein culturing of the human hepatocyte with the at least one inhibitor of MAPK inhibits expression of alpha-fetoprotein (AFP) in the human hepatocyte within five-fold of the level found in fresh primary hepatocytes.

3. The method of claim 1, wherein the inhibitor of MAPK is U0126 or PD0325901.

4. The method of claim 1, wherein the cultured human hepatocyte expresses at least one additional mature hepatic gene that is CYP1A2, CYP2C9, CYP2D6, CYP2E1, CYP3A4, UGT1A1, SLCO1B3 or ALB at an expression level at least 70% of the expression level of the same gene in fresh primary hepatocytes.

5. The method of claim 1, wherein the human hepatocyte is a primary hepatocyte obtained from a liver.

6. The method of claim 1, wherein the human hepatocyte is an immature hepatocyte.

7. The method of claim 6, wherein the immature hepatocyte is a fetal hepatocyte.

8. The method of claim 6, wherein the immature hepatocyte is a cultured liver cancer cell.

9. The method of claim 6, wherein the immature hepatocyte is an immortalized primary hepatic cell.

10. The method of claim 6, wherein after culturing with the least one inhibitor of MAPK, the immature hepatocyte has an at least two-fold reduction in expression of alpha-fetoprotein (AFP) compared to uncultured immature hepatocytes and has become a cultured hepatocyte.

11. The method of claim 6, wherein the method reduces the level of AFP expression in the cultured hepatocyte to an expression level within five-fold of the expression level of AFP found in fresh primary hepatocytes.

* * * * *